(12) United States Patent  (10) Patent No.: US 7,403,816 B2
Ohkura  (45) Date of Patent: Jul. 22, 2008

(54) METHOD AND APPARATUS FOR ANALYZING BIOELECTRICAL RESPONSE WAVEFORM INFORMATION, AND DIAGNOSTIC APPARATUS THEREOF

(76) Inventor: Tamiko Ohkura, 14-12, Inograshira 3-chome, Mitaka-shi, Tokyo 181-0001 (JP)

( * ) Notice: Subject to any disclaimer, the term of this patent is extended or adjusted under 35 U.S.C. 154(b) by 303 days.

(21) Appl. No.: 11/054,436

(22) Filed: Feb. 10, 2005

(65) Prior Publication Data
US 2005/0192510 A1 Sep. 1, 2005

Related U.S. Application Data

(63) Continuation-in-part of application No. 10/468,805, filed as application No. PCT/JP02/01864 on Feb. 28, 2002.

(30) Foreign Application Priority Data
Mar. 1, 2001 (JP) ............................ 2001-56298

(51) Int. Cl.
A61B 5/05 (2006.01)
A61H 39/02 (2006.01)
G01R 25/06 (2006.01)
G01R 27/08 (2006.01)
G01R 27/06 (2006.01)

(52) U.S. Cl. ..................... 600/547; 600/548; 324/608; 324/692; 324/704

(58) Field of Classification Search ................. 600/547, 600/548; 324/608, 691, 692, 704
See application file for complete search history.

(56) References Cited

U.S. PATENT DOCUMENTS
3,971,366 A * 7/1976 Motoyama ................. 600/547
(Continued)

FOREIGN PATENT DOCUMENTS
JP 62-324 A 1/1987
(Continued)

OTHER PUBLICATIONS

T. Ohkura, et al, "Scientific Research on Oriental Medicine (V) AMI Study on Evaluation of the Effects of Kampo Medicines," Journal of Traditional Medicines 15, 264-165, 1998. ISSN 1340-6302.

(Continued)

*Primary Examiner*—Max Hindenburg
*Assistant Examiner*—John Pani
(74) *Attorney, Agent, or Firm*—Mattingly, Stanger, Malur & Brundidge, PC

(57) ABSTRACT

A method for analyzing skin response waveform information obtained by measuring skin impedance with a voltage of a predetermined frequency. A current value at the start of polarization caused by the application of the voltage is determined, followed by determining a current value after a predetermined amount of time from the start of the polarization. A current value after termination of the polarization (value NT) is then determined and the difference between the current value at the start of the polarization and after the predetermined amount of time from the start of the polarization (value A) is determined. The difference between the current value after the predetermined amount of time from the start of the polarization and the value NT (value B) is determined, followed by analyzing the skin response waveform information using the ratios A/B, B/A and the value NT.

8 Claims, 21 Drawing Sheets

U.S. PATENT DOCUMENTS 4,557,271 A * 12/1985 Stoller et al. ................. 600/547
4,794,934 A * 1/1989 Motoyama et al. ........... 600/547
5,427,113 A * 6/1995 Hiroshi et al. ............... 600/547

FOREIGN PATENT DOCUMENTS

| | | |
|---|---|---|
| JP | 62-148645 A | 7/1987 |
| JP | 2-59730 | 12/1990 |
| JP | 8-38437 A | 2/1996 |
| JP | 8-168469 A | 7/1996 |

OTHER PUBLICATIONS

M. Kido, "Meridan Measurement of Qi-Gong Operation and Synchronous Phenomena," Journal of Mind-Body Science, vol. 2, No. 1 Apr. 1993. ISSN 0918-2489.

* cited by examiner

FIG.3
NORMAL PERSON
(a)
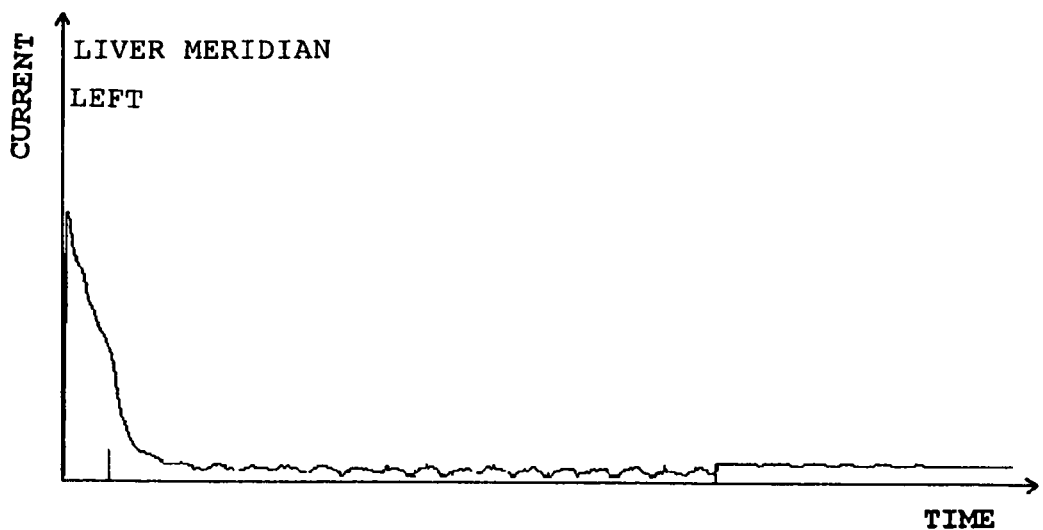
(b)
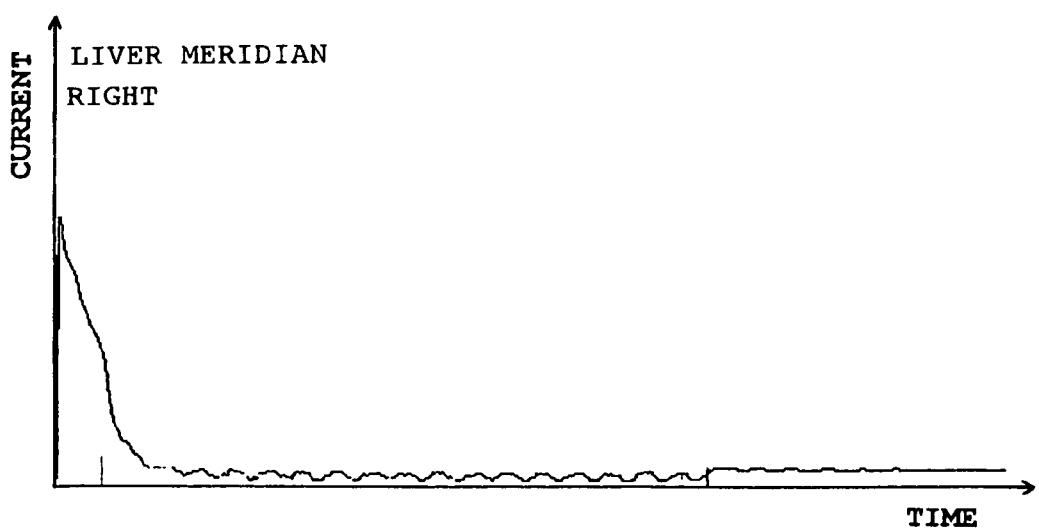

FIG.4
NORMAL PERSON
(a)
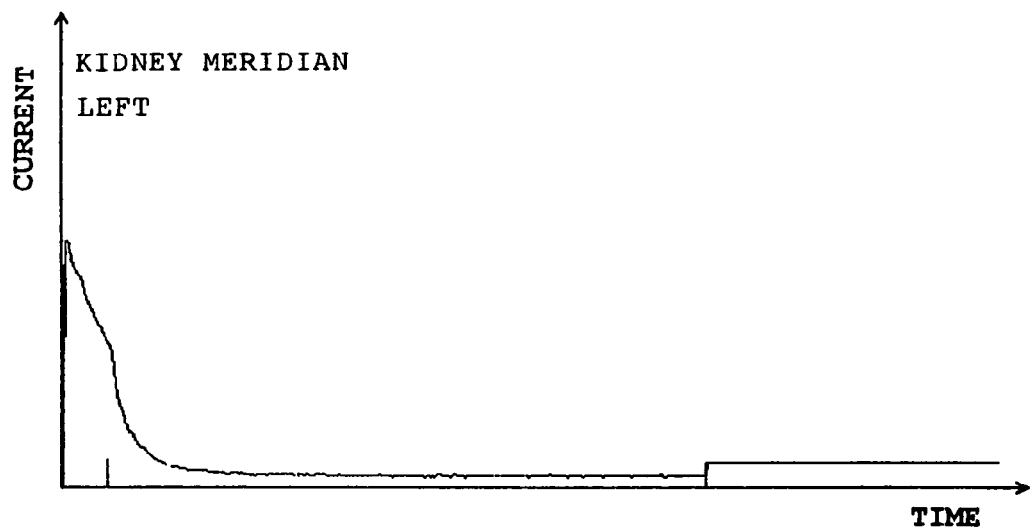
(b)
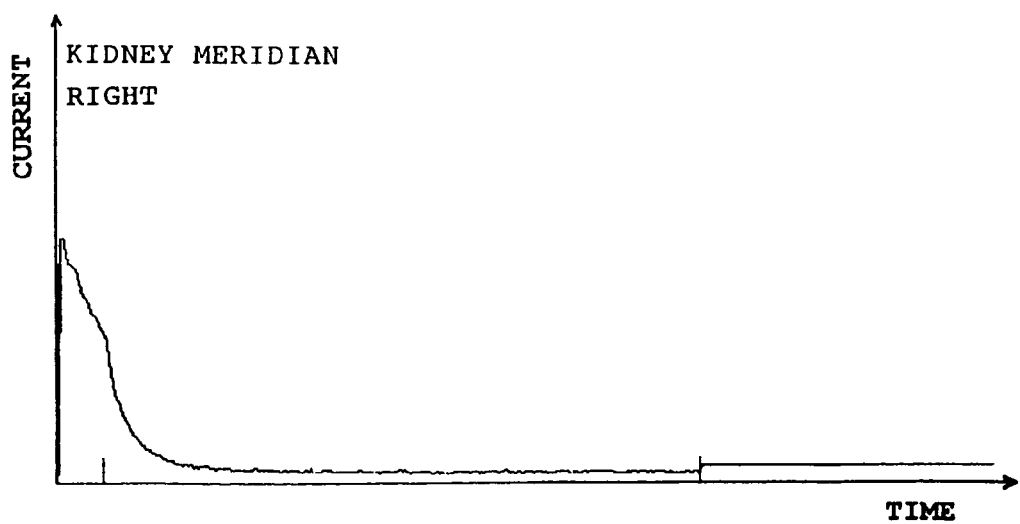

FIG.5
(a) ABNORMAL PERSON
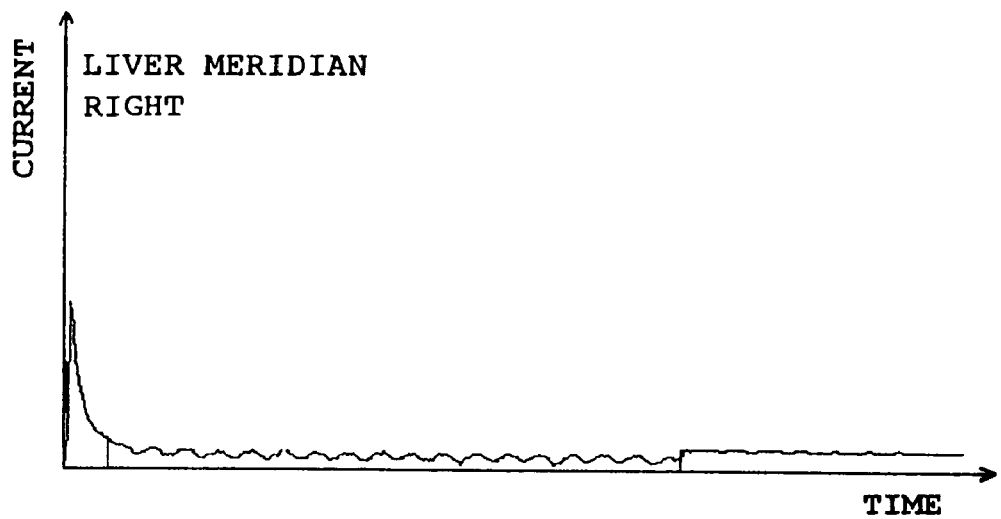
(b)
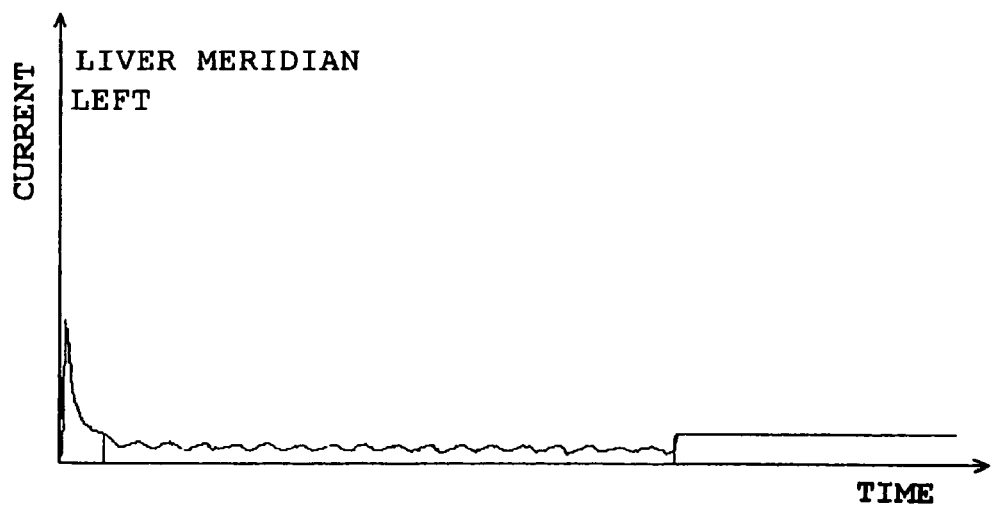

FIG.6
(a)
ABNORMAL PERSON
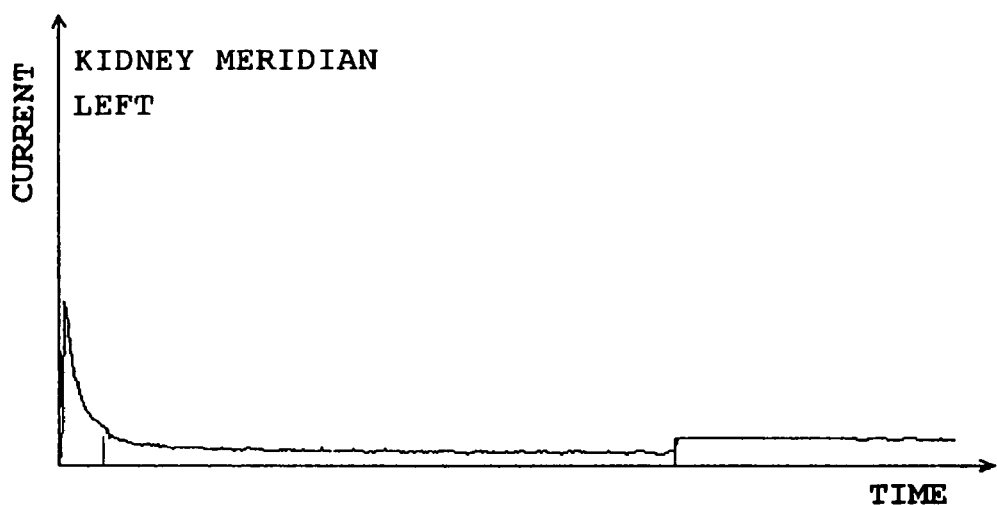
(b)
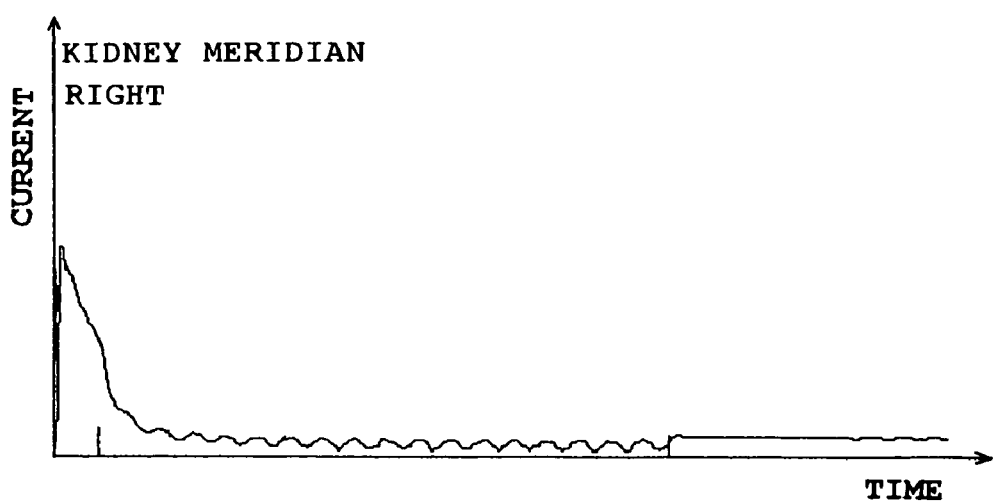

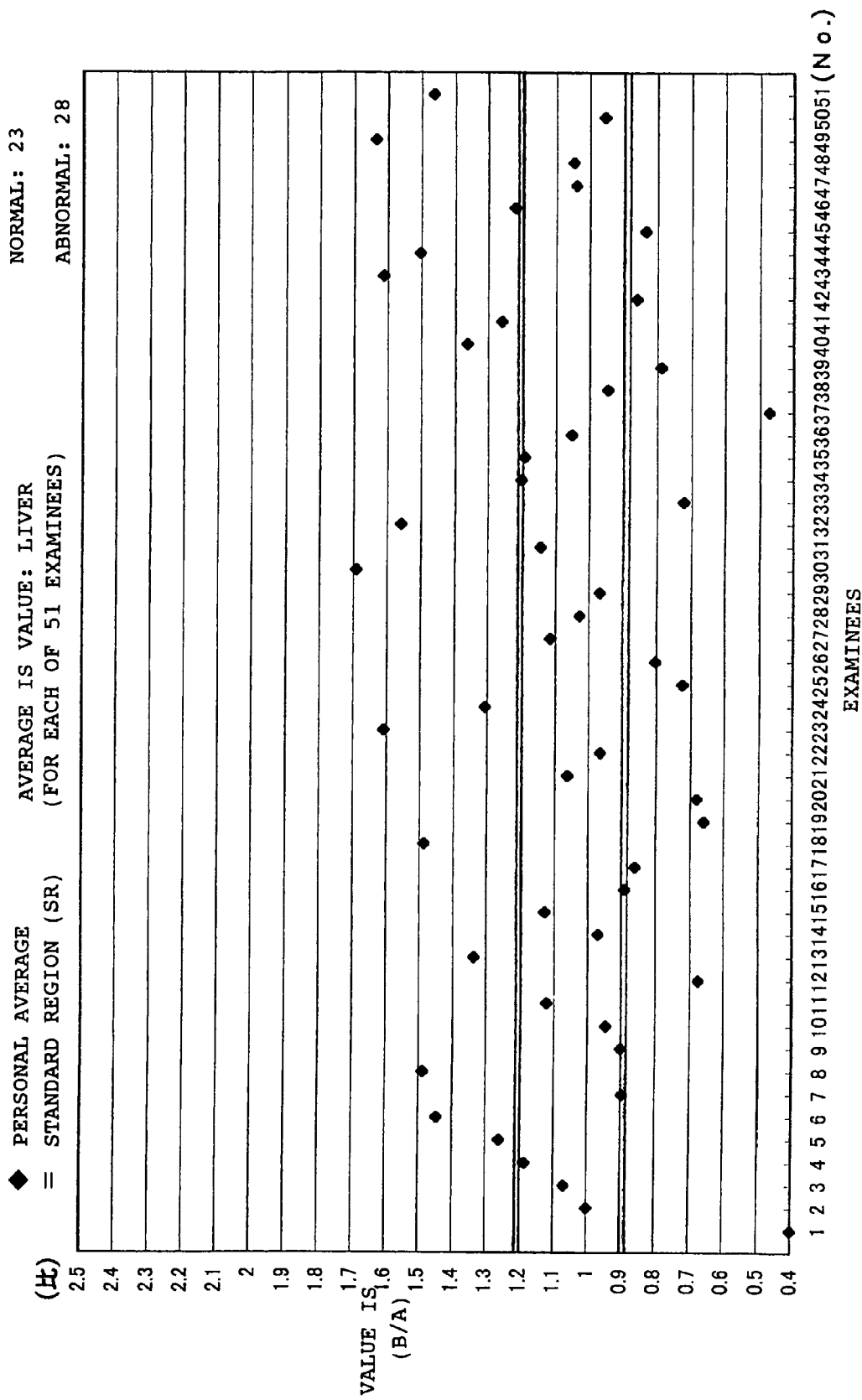

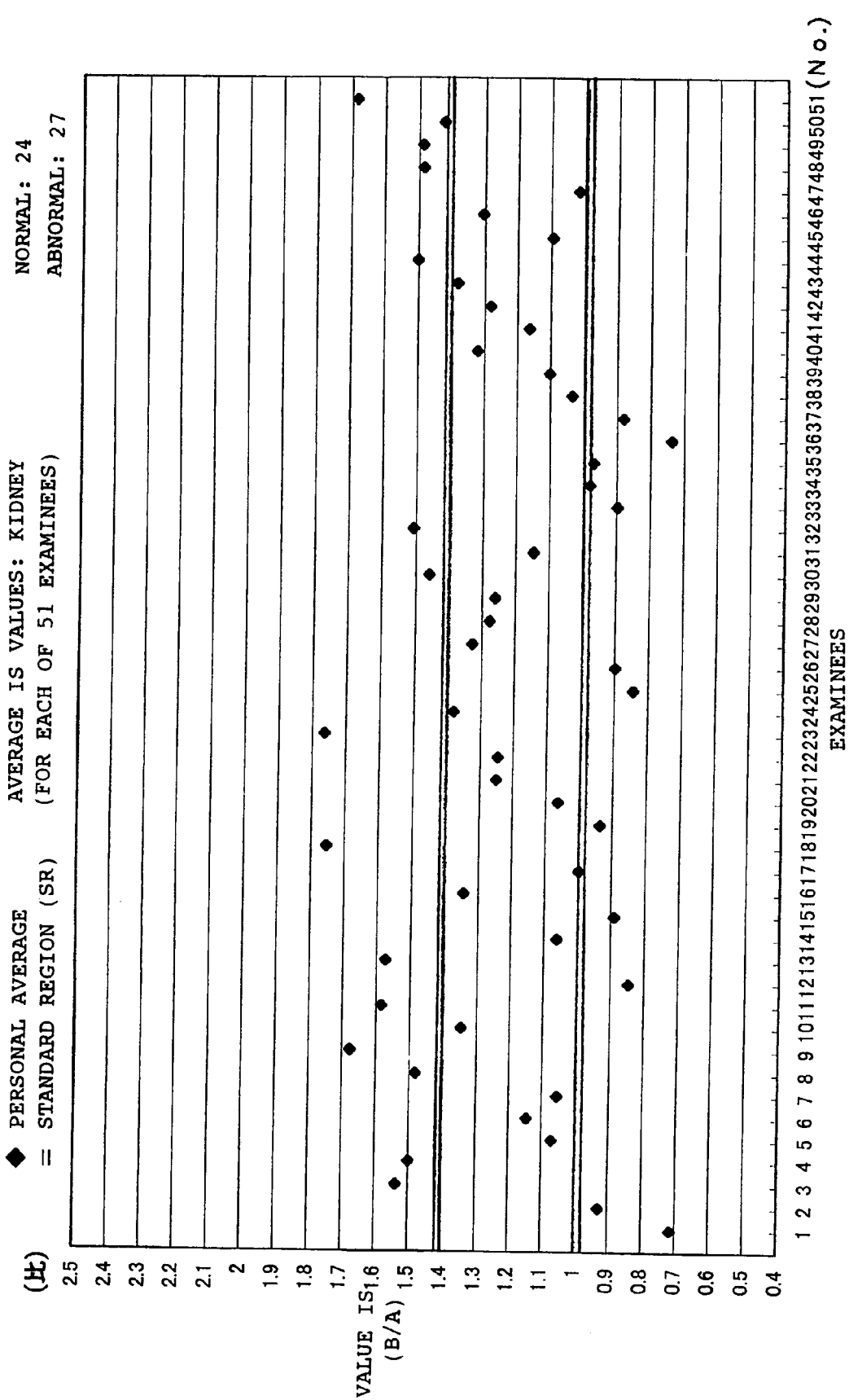

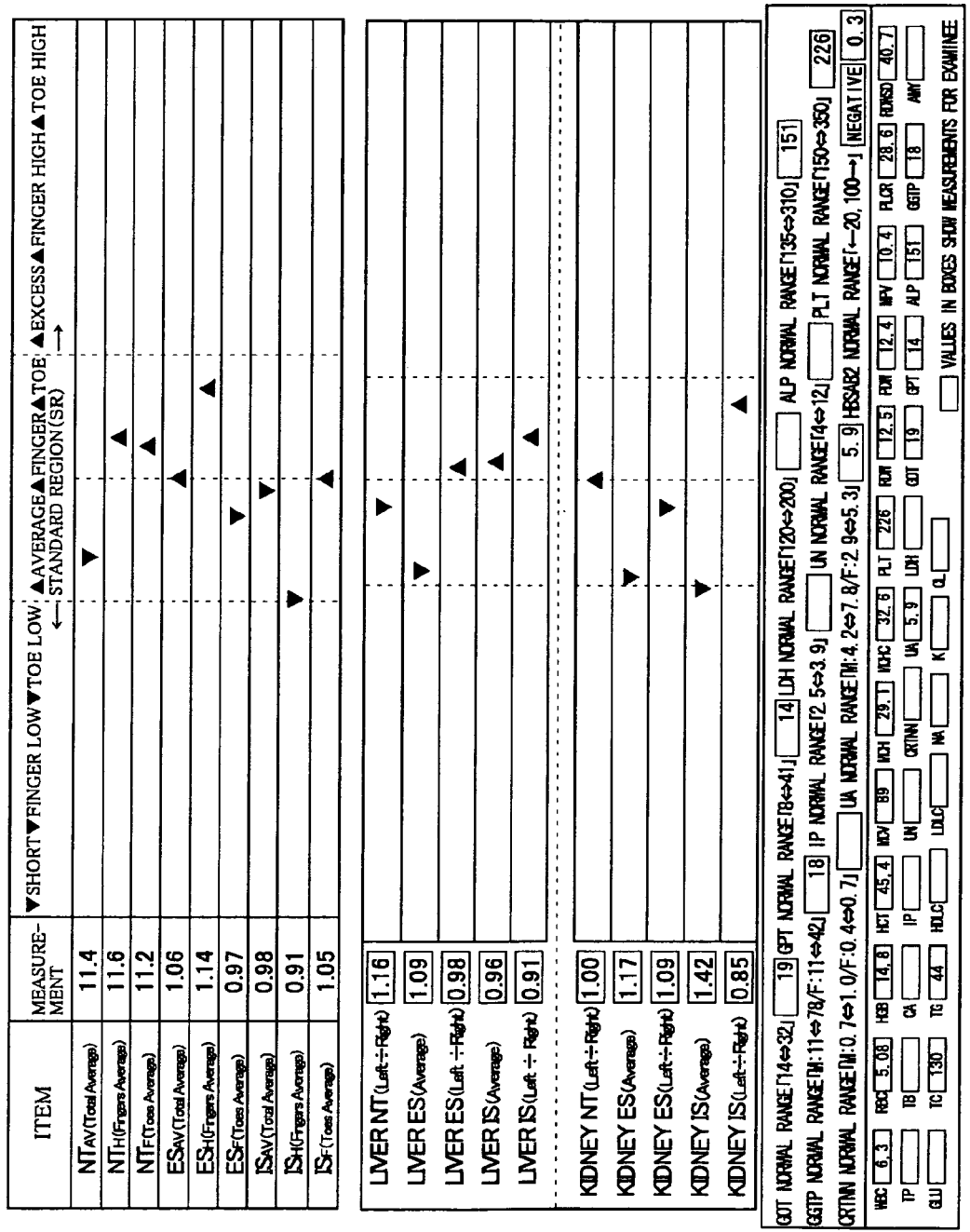

FIG.19
TOTAL EVALUATION FOR DISEASED PERSON AND THE PERSON'S CLINICAL EXAMINATION DATA IN WESTERN MEDICINE

| ITEM | MEASURE-MENT | ▼SHORT ▼FINGER LOW ▼TOE LOW; ▲AVERAGE ▲FINGER▲TOE; ▲EXCESS▲FINGER HIGH▲TOE HIGH ←—STANDARD REGION(SR)—→ | | |
|---|---|---|---|---|
| NTAV(Total Average) | 33.6 | | | ▲ |
| NTH(Fingers Average) | 42.5 | | | ▲ |
| NTF(Toes Average) | 24.7 | | ▲ | |
| ESAV(Total Average) | 1.60 | | | ▲ |
| ESH(Fingers Average) | 0.85 | | ▲ | |
| ESF(Toes Average) | 2.36 | | | ▲ |
| ISAV(Total Average) | 1.00 | | ▲ | |
| ISH(Fingers Average) | 1.56 | | | ▲ |
| ISF(Toes Average) | 0.64 | ▶ | | |

| | | | | |
|---|---|---|---|---|
| LIVER NT (Left÷Right) | 0.37 | | | |
| LIVER ES (Average) | 5.83 | | | ▲ |
| LIVER ES (Left÷Right) | 0.98 | | | |
| LIVER IS (Average) | 0.17 | ▶ | | |
| LIVER IS (Left÷Right) | 0.99 | | | |
| KIDNEY NT (Left÷Right) | 0.97 | | | |
| KIDNEY ES (Average) | 2.93 | | ▲ | |
| KIDNEY ES (Left÷Right) | 4.62 | | | ▲ |
| KIDNEY IS (Average) | 0.71 | ▶ | | |
| KIDNEY IS (Left÷Right) | 0.21 | | | |

GOT NORMAL RANGE[8↔41] [196] GPT NORMAL RANGE[8↔41] [305] LDH NORMAL RANGE[120↔200] [347] ALP NORMAL RANGE[135↔310] [440]
GGTP NORMAL RANGE[M:11↔78/F:11↔42] [782] IP NORMAL RANGE[2.5↔3.9] [3] UN NORMAL RANGE[4↔12] [9.5] PLT NORMAL RANGE[150↔350] [279]
CRTNN NORMAL RANGE[M:0.7↔1.0/F:0.4↔0.7] [0.9] UA NORMAL RANGE[M:4.2↔7.8/F:2.9↔5.3] [9] HESAB2 NORMAL RANGE[--,20,100--] [NEGATIVE] [25.8]

| RBC | 7.5 | RBC | 4.56 | HGB | 15.3 | HCT | 46.8 | MCV | 103 | MCH | 33.6 | MCHC | 32.7 | PLT | 279 | RDW | 13.3 | MPV | 11.5 | PLCR | 10.3 | RDWSD | 49.9 |
| IP | 6.9 | TB | 0.8 | CA | 8.7 | UN | 3 | LN | 9.5 | CRTNN | 0.9 | UA | 9 | LDH | 347 | GOT | 196 | GPT | 305 | ALP | 440 | GGTP | 782 | AMY | 82 |
| GLU | 81 | TC | 252 | TG | 770 | HDLC | 59 | LDLC | 57 | | | NA | 138.1 | K | 3.6 | CL | 98 | | | | | | | | | | |

□ VALUES IN BOXES SHOW MEASUREMENTS FOR EXAMINEE

FIG.20
- Prior Art -

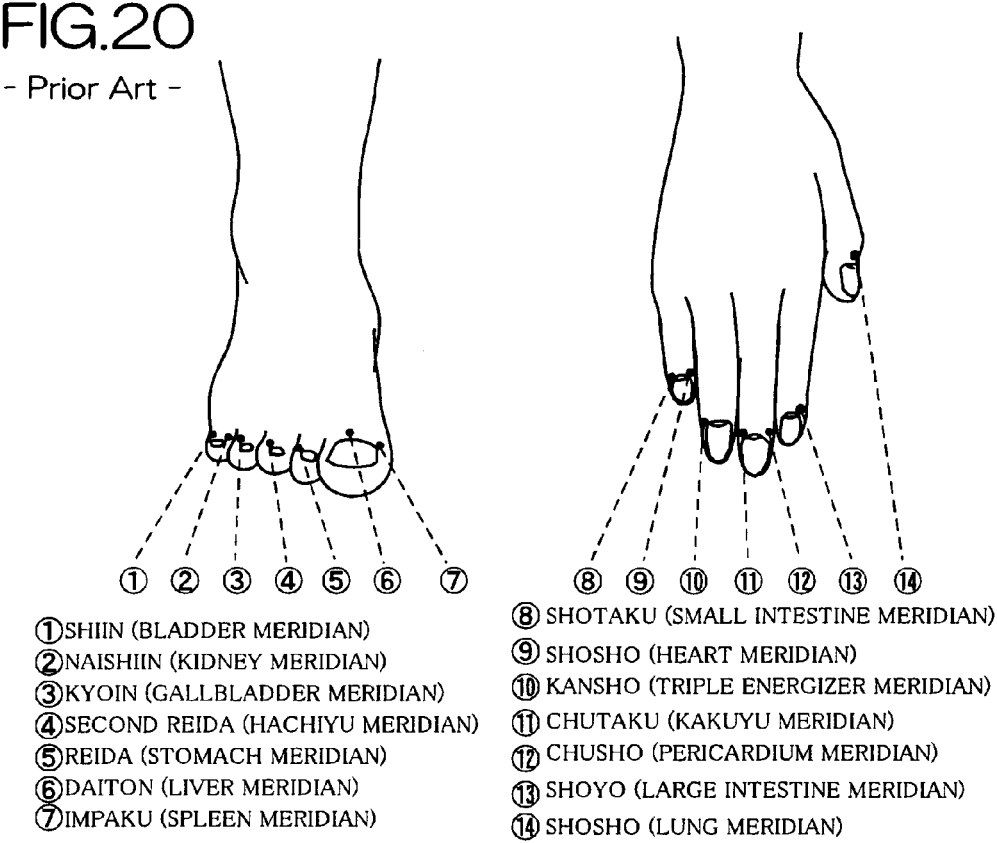

① SHIIN (BLADDER MERIDIAN)
② NAISHIIN (KIDNEY MERIDIAN)
③ KYOIN (GALLBLADDER MERIDIAN)
④ SECOND REIDA (HACHIYU MERIDIAN)
⑤ REIDA (STOMACH MERIDIAN)
⑥ DAITON (LIVER MERIDIAN)
⑦ IMPAKU (SPLEEN MERIDIAN)

⑧ SHOTAKU (SMALL INTESTINE MERIDIAN)
⑨ SHOSHO (HEART MERIDIAN)
⑩ KANSHO (TRIPLE ENERGIZER MERIDIAN)
⑪ CHUTAKU (KAKUYU MERIDIAN)
⑫ CHUSHO (PERICARDIUM MERIDIAN)
⑬ SHOYO (LARGE INTESTINE MERIDIAN)
⑭ SHOSHO (LUNG MERIDIAN)

FIG.21
- Prior Art -

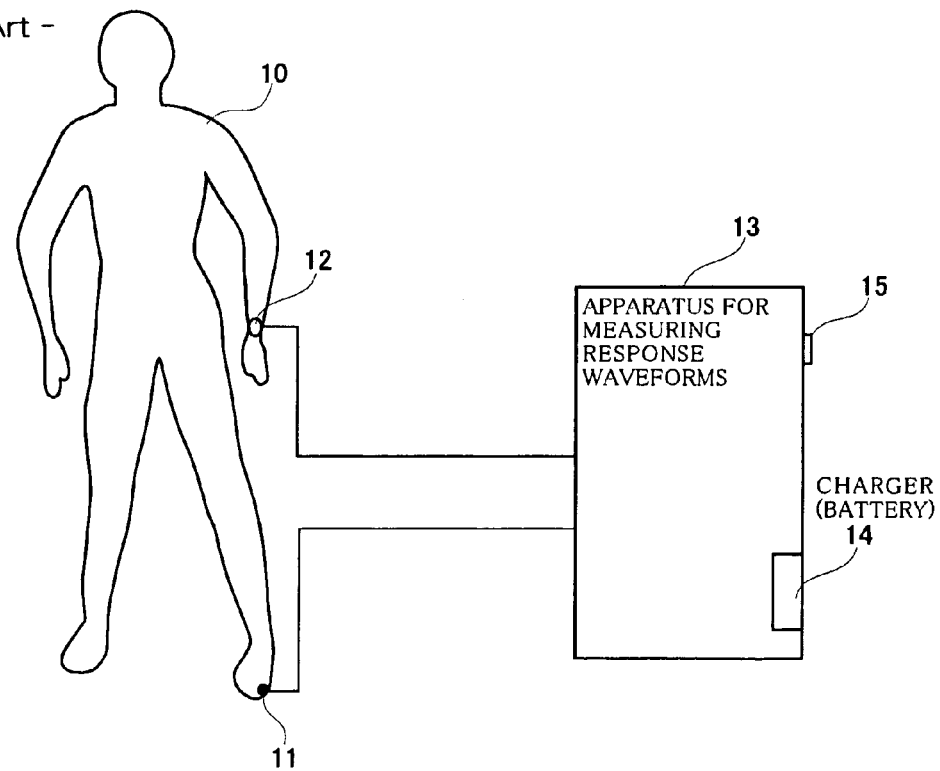

US 7,403,816 B2

METHOD AND APPARATUS FOR ANALYZING BIOELECTRICAL RESPONSE WAVEFORM INFORMATION, AND DIAGNOSTIC APPARATUS THEREOF

CROSS-REFERENCE TO RELATED APPLICATION

This application is a continuation-in-part of U.S. application Ser. No. 10/468,805 entitled "METHOD AND APPARATUS FOR ANALYZING BIOELECTRICAL RESPONSE WAVEFORM INFORMATION, AND DIAGNOSTIC APPARATUS THEREOF", filed on Mar. 4, 2004, by Tamiko OHKURA, the contents of which are herein incorporated by reference, which application is a 371 of PCT/JP02/01864 filed on Feb. 28, 2002, and claims priority benefits of Japanese Patent Application No. 2001-56298 filed Mar. 1, 2001.

TECHNICAL FIELD

The present invention relates to a method and apparatus for analyzing-skin response waveform information obtained by measuring skin impedance with a voltage of a predetermined frequency, as well as an apparatus for performing a diagnosis on a body using the method and apparatus. More particularly, the invention relates to a technique for performing an analysis with three parameters of values ES, IS, and NT of the response waveform information, as well as an apparatus for performing a diagnosis on a body using the technique.

BACKGROUND ART

Noninvasive means to evaluate functional conditions of a whole body such as functionality of autonomic nerves and internal organs by measuring meridians in Oriental medicine, what is provisionally called AMI (Apparatus for Measuring the Function of the Meridians and Their Corresponding Internal Organs) is being developed. One example is an apparatus for processing route-organ functional information described in Patent No. 1634716 (Japanese Patent Publication No. 2-59730).

Also, a research on evaluation of medicinal effects of Chinese medicines using the skin impedance (AMI) method (Tamiko Ohkura, et al.) has been reported in "Journal of Traditional Medicines (Wakan-Iyakugaku-Zasshi) 15,264, 1998."

Conventional apparatus for measuring response waveforms of a body according to the skin impedance (AMI) method use a different electrode and an indifferent electrode. As shown in FIG. 21, a different electrode 11 is attached to one of 28 "Seiketsu" measurement points (see FIG. 20) on a body 10, and an indifferent electrode 12 is attached to either wrist. A weak, single rectangular low voltage pulse is applied, and its output is supplied to an apparatus for measuring response waveforms 13 to be amplified. Then, a response waveform I is retrieved from an output terminal 15. In FIG. 21, reference numeral 14 denotes a charger.

As shown in FIG. 22, a parameter BP corresponding to the flow of "Qi", a parameter IQ for defense functionality (integral value), and a parameter AP associated with autonomic nerves are defined based on a response waveform Iw measured with the skin impedance (AMI) method. In this regard, a report entitled "Synchronous phenomenon of Qigong in measurement of meridians" has been made (see Journal of Mind-Body Science (Jintai-Kagaku) 2-(1): 19 to 29, 1993). The report describes a phenomenon that the value of the parameter AP increases with tension of the sympathetic nerves and decreases when the parasympathetic nerves or the vagus nerves are dominant.

Also, an apparatus for performing a diagnosis on a body that measures a surface potential of a body and performs a diagnosis on the body based on the measured surface potential has been disclosed (see Japanese Patent Laid-Open No. 8-38437).

By reviewing these prior techniques, the inventor has found the fact as follows. The response waveform Iw measured with the skin impedance (AMI) method shown in FIG. 22 involves the phenomenon that the value of the parameter AP increases with tension of the sympathetic nerves and decreases when the parasympathetic nerves or the vagus nerves are dominant. All of the above techniques define the waveform Iw with the above mentioned three parameters, and in particular define BP as a value at a single point before polarization. Therefore, BP has instability and a low precision and varies greatly due to personal differences and conditions of the measuring environment (especially seasonal variation). Furthermore, since IQ depends on the value of BP and affects the integral value, it has a low precision and may not always reflect the body correctly.

The object of the present invention is to provide a method and apparatus for analyzing response waveform information capable of being applied to uses such as a diagnosis on a body.

Another object of the present invention is to provide a diagnostic apparatus for a body capable of performing a diagnosis on a body based on the analysis of the response waveform information.

The above and other objects of the present invention, as well as its novel features will be apparent from the description herein and the appended drawings.

DISCLOSURE OF THE INVENTION

The present invention disclosed herein may be briefly described as follows.

A first aspect of the present invention is an apparatus for analyzing bioelectrical response waveform information obtained from measurements of skin impedance measured by applying a pulse voltage to a body. The apparatus is characterized by comprising: first means for determining a current value P1 when a current is at its peak upon application of the pulse voltage; second means for determining a current value P2 after a predetermined amount of time (i.e., the time that elapses before a characteristic point at which a dermis layer and epidermis begin to electrically mix) from the current peak time; a third means for determining a current value NT when a current reaches an equilibrium state with a further elapse of time after the predetermined amount of time (i.e., the time that elapses before a characteristic point at which a dermis layer and epidermis begin to electrically mix) from the current peak time; fourth means for determining a difference A between the current values P1 and P2; fifth means for determining a difference B between the current values P2 and NT; and sixth means for analyzing bioelectrical response waveform information by using three values as parameters, two of the three values being ratios A/B=ES and B/A=IS between the values A and B determined by the fourth and fifth means respectively, and the third value being NT.

A second aspect of the present invention is an apparatus for performing a diagnosis on a body that analyzes bioelectrical response waveform information obtained from measurements of skin impedance measured by applying a pulse voltage to the body and performs a diagnosis on the body based on the analysis of the bioelectrical response waveform information. The apparatus is characterized by comprising: first means for determining a current value P1 when a current is at its peak upon application of the pulse voltage; second means for determining a current value P2 after a predetermined amount of time from the current peak time; third means for determining a current value NT when a current reaches an equilibrium state with a further elapse of time after a predetermined amount of time (i.e., the time that elapses before a characteristic point at which a dermis layer and epidermis begin to electrically mix) from the current peak time; fourth means for determining a difference A between the current values P1 and P2; fifth means for determining a difference B between the current values P2 and NT; sixth means for analyzing bioelectrical response waveform information by using three values as parameters, two of the three values being ratios A/B=ES and B/A=IS between the values A and B determined by the fourth and fifth means respectively, and the third value being NT; and seventh means for comparing and associating a result of analysis of the bioelectrical response waveform information outputted from the sixth means with stored clinical examination data.

A third aspect of the present invention is an apparatus for analyzing bioelectrical response waveform information obtained from measurements of skin impedance measured by applying a pulse voltage to a body. The apparatus is characterized by comprising: first means for determining a current value P1 at 600 ns, when a current is at its peak upon application of the pulse voltage; second means for determining a current value P2 after 4 µs (i.e., the time that elapses before a characteristic point at which a dermis layer and epidermis begin to electrically mix) from the current peak time upon application of the pulse voltage; third means for determining a current value NT after 256 µs when a current reaches an equilibrium state with a further elapse of time after 4 µs from the current peak time; fourth means for determining a difference A between the current values P1 and P2; fifth means for determining a difference B between the current values P2 and NT; and sixth means for analyzing bioelectrical response waveform information by using three values as parameters, two of the three values being ratios A/b=ES and B/A=IS between the values A and B determined by the fourth and fifth means respectively, and the third value being NT.

In a fourth aspect of the present invention, the apparatus for analyzing bioelectrical response waveform information according to any one of the first to three aspects is characterized in that at least one of a measurement, an average of measurements, a ratio between measurements of right and left, or a ratio between measurements of hands and feet of a bioelectrical response waveform of a body or part of a body is used for each of the values ES, IS, and NT.

A fifth aspect of the present invention is an apparatus for performing a diagnosis on a body that analyzes bioelectrical response waveform information obtained from measurements of skin impedance measured by applying a pulse voltage to the body and performs a diagnosis on the body based on the analysis of the bioelectrical response waveform information. The apparatus is characterized by comprising: first means for determining a current value P1 at 600 ns, when a current is at its peak upon application of the pulse voltage; second means for determining a current value P2 after 4 µs (i.e., the time that elapses before a characteristic point at which a dermis layer and epidermis begin to electrically mix) from the current peak time upon application of the pulse voltage; third means for determining a current value (NT after 256 µs when a current reaches an equilibrium state with a further elapse of time after 4 µs from the current peak time; fourth means for determining a difference (A between the current values P1 and P2; fifth means for determining a difference B between the current values P2 and NT; sixth means for analyzing bioelectrical response waveform information by using three values as parameters, two of the three values being ratios A A/B=ES and B/A=IS between the values A and B determined by the fourth and fifth means respectively, and the third value being NT; and seventh means for comparing and associating a result of analysis of the bioelectrical response waveform information outputted from the sixth means with stored clinical examination data.

In a sixth aspect of the present invention, the apparatus for performing a diagnosis on a body based on bioelectrical response waveform information according to the fifth aspect is characterized in that at least one of a measurement, an average of measurements, a ratio between measurements of right and left, or a ratio between measurements of hands and feet of a bioelectrical response waveform of a body or part of a body is used for each of the values ES, IS, and NT.

According to the present invention, a response waveform provided by an apparatus for measuring bioelectrical response waveforms can be analyzed and computed to produce the three parameters of values ES, IS, and NT.

The three parameters of values ES, IS, and NT produced can be combined to perform various diagnoses. That is, the three parameters of values ES, IS, and NT can be combined to create values that may indicate the condition of a whole body, the condition of the respiratory and circulatory system, the condition of each organ system, the conditions of the right side and the left side, and increase or decrease in functionality of each internal organ. The values may be used to locate diseased parts and to quantify systemic functional conditions including neurological manifestations. This enables diagnoses according to correlation with nervous system relevant to body control functions (neurotransmitter), the endocrine and metabolism system (hormone), and the immune system (cytokine).

Furthermore, since the present invention enables noninvasive prediction of diseases, it is especially effective when applied to regular measurement to facilitate an efficient primary prophylaxis for keeping health, as well as to a medical checkup for diseases.

With reference to the drawings, the present invention will be described below according to its embodiments (implementations).

BRIEF DESCRIPTION OF THE DRAWINGS

FIG. 3 is a waveform diagram showing response waveform information (data) on the liver meridian of a normal person according to the embodiment 1;

FIG. 4 is a waveform diagram showing response waveform information (data) on the kidney meridian of a normal person according to the embodiment 1;

FIG. 5 is a waveform diagram showing response waveform information (data) on the liver meridian of a diseased person according to the embodiment 1;

FIG. 6 is a waveform diagram showing response waveform information (data) on the kidney meridian of a diseased person according to the embodiment 1;

FIG. 16 is a diagram showing average IS values resulted from waveform analysis of the liver meridian according to the embodiment 2;

FIG. 17 is a diagram showing average IS values resulted from waveform analysis of the kidney meridian according to the embodiment 2;

FIG. 18 is a diagram showing total evaluation for a normal person according to the embodiment 2, as well as the person's clinical examination data in terms of Western medicine;

FIG. 19 is a diagram showing total evaluation for a diseased person according to the embodiment 2, as well as the person's clinical examination data in terms of Western medicine;

FIG. 20 is a diagram showing 14 conventional "Seiketsu" measurement points on a hand and a foot of a body;

FIG. 21 is a diagram showing a schematic configuration of a conventional apparatus for measuring bioelectrical response waveforms (apparatus for measuring skin impedance)

BEST MODE FOR CARRYING OUT THE INVENTION

Embodiment 1

Figure 1:
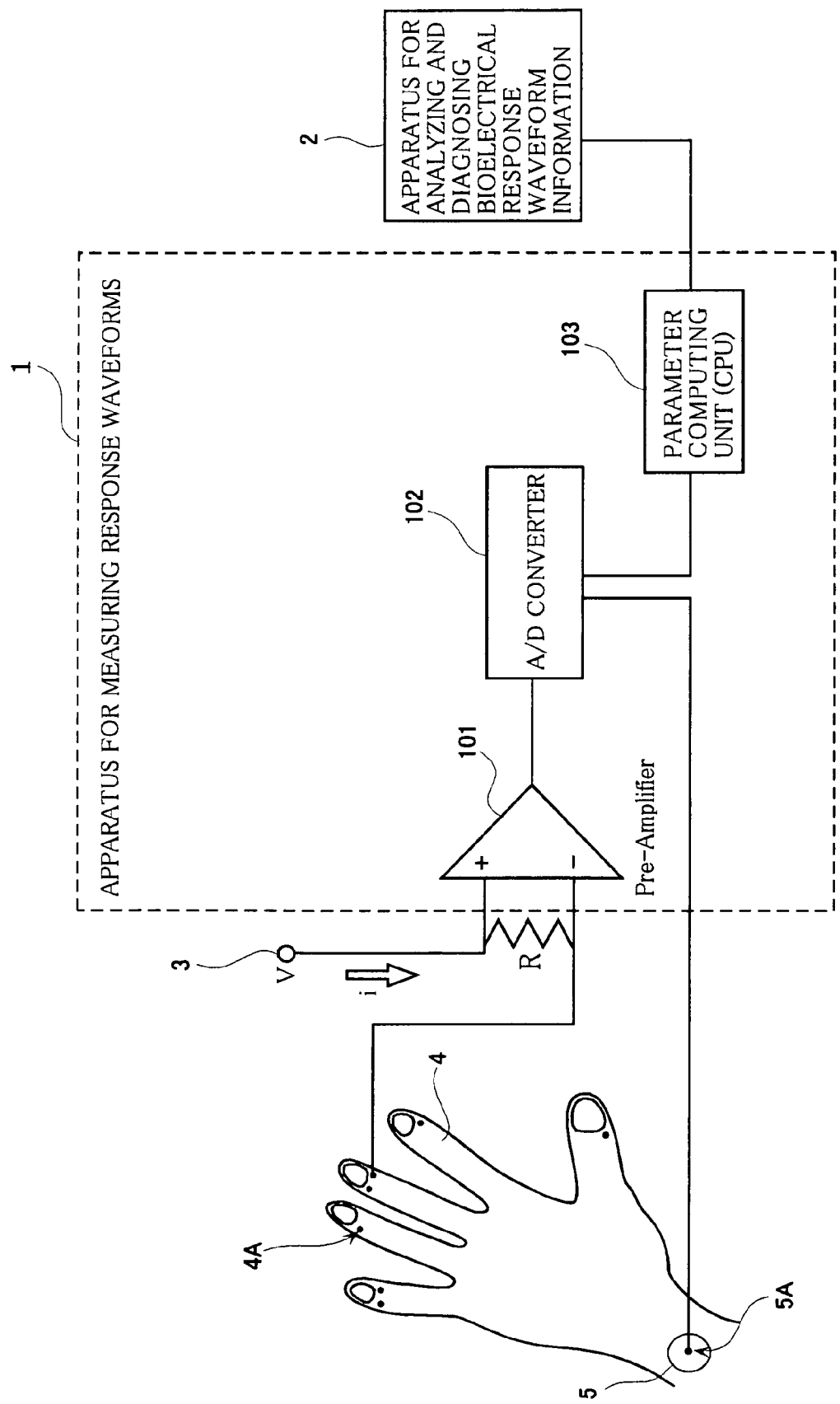
FIG. 1 is a functional block diagram of an apparatus for measuring bioelectrical response waveforms according to an embodiment (implementation) 1 of the present invention.

FIG. 1 is a functional block diagram of an apparatus for measuring bioelectrical response waveforms according to an embodiment (implementation) 1 of the present invention.

As shown in FIG. 1, the apparatus for measuring bioelectrical response waveforms 1 according to the embodiment 1 includes a current amplifier (Pre-Amplifier) 101, an A/D converter 102, and parameter computing unit (CPU) 103.

Figure 2:
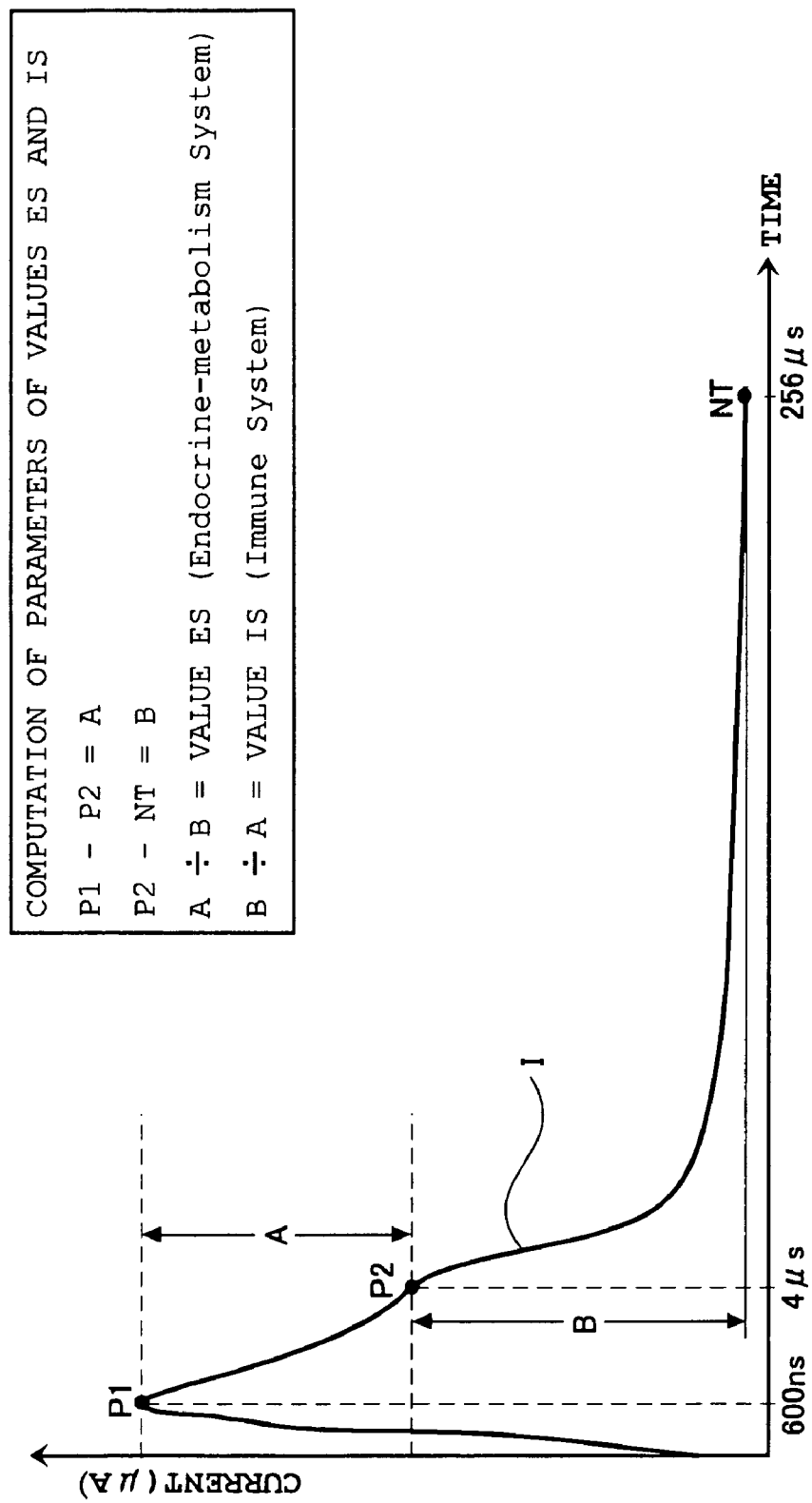
FIG. 2 is a response waveform diagram showing a response waveform according to the embodiment 1.

For example, the apparatus for measuring bioelectrical response waveforms 1 according to the embodiment 1 has a silver-gel different electrode 4A of 7 mm square attached to a meridian point on a finger 4, and a dish-shaped electrode (indifferent electrode for electrocardiograms) 5A attached to a wrist 5. A pulse voltage V (e.g., a pulse voltage of 3 volts with a cycle period of 256 μs) is applied with a predetermined cycle period (e.g., a frequency of 1 MHz) by a power supply 3 through a resistor R. This allows a polarization current (μA) to flow between the silver-gel different electrode 4A and the dish-shaped electrode (indifferent electrode for electrocardiograms) 5A, resulting in a response waveform (information) I as shown in FIG. 2. The response waveform (information) I is amplified by the current amplifier (pre-amplifier) 101 and converted into a digital signal by the A/D converter 102. The digital signal is input to the parameter computing unit (CPU) 103. As shown in FIG. 2, the parameter computing unit (CPU) 103 determines a current value P1 at 600 ns, when a current is at its peak upon application of the pulse voltage in the response waveform information I. It then determines a current value P2 after 4 μs (which is the time that elapses before a characteristic point at which a dermis layer and epidermis begin to electrically mix) from the current peak upon application of the pulse voltage. It then determines a current value NT after 256 μs when a current reaches an equilibrium state with a further elapse of time after the 4 μs from the current peak.

Next, the difference A between the values P1 and P2 (P1−P2=A) and the difference B between the values P2 and NT (P2−NT=B) are determined. From the values A and B obtained respectively, the ratios between them are determined, that is, A/B=ES and B/A=IS. These values ES and IS and the previously determined value NT may be used as three parameters for providing information for analyzing skin response waveform information. The obtained parameter information on the values ES, IS, and NT is output to an apparatus for analyzing and diagnosing response waveform information 2.

By adopting the ratios between the values A and B, that is, A/B=ES and B/A=IS, it is able to constantly provide stable values unaffected by variances of the response waveform information I due to personal differences or varying conditions of the measuring environment depending on the season, and so on. This results in an increased reliability of diagnoses.

With respect to FIG. 2, when skin impedances were measured with a frequency of 1 MHz, the captured waveforms always showed the characteristics of a sudden temporary increase at 600 ns, a subsequent linear (sharp) decrease and a gentle falling curve and a decrease at 4 μs. These characteristics that a current changes in the period from 600 ns to 4 μs are utilized and a difference A between the current value P1 at 600 ns and the current value P2 at 4 μs is regarded as a polarization property and a decrease in the current starting at 4 μs and ending at leak resistance in the epidermis is regarded as a change in the resistance after the polarization property (i.e., a difference in ion distribution of the intra- and extra-cellular fluids in the dermis layer) and is represented with a difference B between the current value P2 at 4 us and the current value NT at leak resistance. The measurement was rendered at every 1 μs during the period from 21 μs to 100 μs and omitted for the period thereafter. These periods showed a gentle falling curve leading to a leak resistance of epidermis. This decrease over these periods was taken as representation of the difference in ion distribution of the intra- and extra-cellular fluids in the dermis layer (change in the resistance after the polarization property).

Now, response waveform information (data) of a normal person and a diseased person will be shown.

FIG. 3 shows response waveform information (data) on the liver meridian of a normal person, in which (a) is that for the left hand and (b) is that for the right hand.

FIG. 4 shows response waveform information (data) on the kidney meridian of a normal person, in which (a) is that for the left hand and (b) is that for the right hand.

FIG. 5 shows response waveform information (data) on the liver meridian of a diseased person, in which (a) is that for the left hand and (b) is that for the right hand.

FIG. 6 shows response waveform information (data) on the kidney meridian of a diseased person, in which (a) is that for the left hand and (b) is that for the right hand.

Here, 1) the polarization property (difference between 600 ns and 4 μs) is defined as the value "ES (Endocrine-metabolism System)", which represents endocrine and metabolism.

Further, 2) the leak resistance in the dermis layer is defined as the value "NT (Neuro-Transmission)", which represents the autonomic nervous system (transmission system).

Further, 3) the change in the resistance after the polarization property (difference between 4 μs and the leak resistance) is defined as "IS (Immune-System)", which represents the immune system (cytokine).

The response waveform information (data) of a normal person of FIG. 3 and that of FIG. 4 show clear similarities and correlations to each other. However, they show distinct differences from the response waveform information (data) of a diseased person of FIGS. 5 and 6.

Now, the steps of analyzing and computing the parameters in the parameter computing unit (CPU) 103 will be described.

Figure 7:
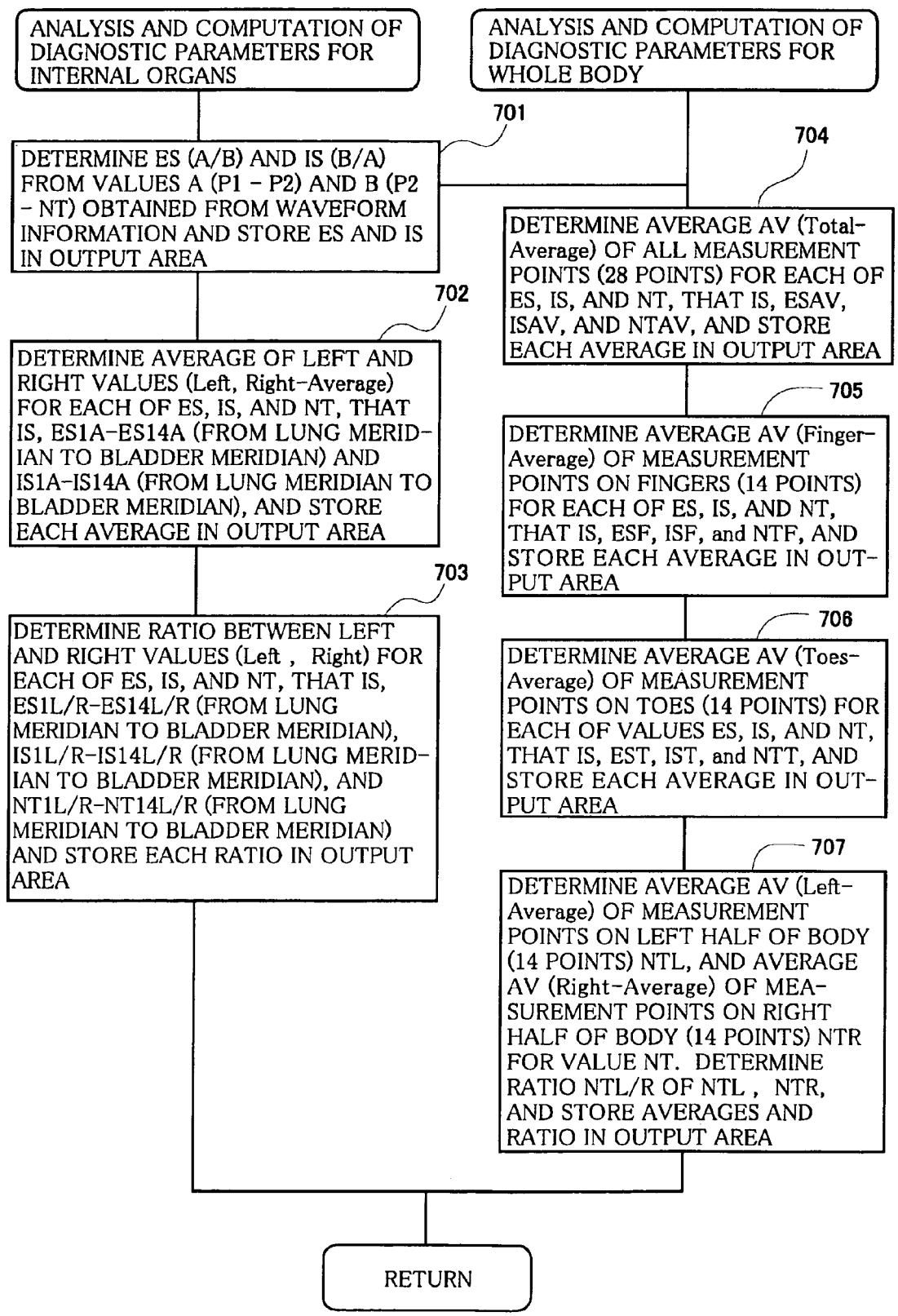
FIG. 7 is a flowchart showing the steps of analyzing and computing diagnostic parameters according to the embodiment 1.

For example, as shown in FIG. 7, the steps of analyzing and computing diagnostic parameters are taken for internal organs and for a whole body.

(Analysis and computation of diagnostic parameters for internal organs).

From the values A (P1-P2) and B (P2-NT) obtained from the waveform information, the values ES (A/B) and IS (B/A) are determined and stored in an output area (step 701).

Then, the average of left and right values (Left Right Average) for each of the values ES and IS, that is, $ES_{1A}$ to $ES_{14}$ (from the lung meridian to the bladder meridian) and $IS_{1A}$ to $IS_{14}$ (from the lung meridian to the bladder meridian) are determined and stored in the output area (step 702).

Then, the ratio between the left and right values (Left÷Right) for each of the values ES, IS, and NT, that is, $ES_{1L/R}$ to $ES_{14L/R}$ (from the lung meridian to the bladder meridian), $IS_{1L/R}$ to $IS_{14L/R}$ (from the lung meridian to the bladder meridian), and $NT_{1L/R}$ to $NT_{14L/R}$ (from the lung meridian to the bladder meridian) are determined and stored in the output area (step 703).

(Analysis and computation of diagnostic parameters for a whole body)

The average AV (Total Average) of all measurement points (e.g., 28 points) for each of the values ES, IS, and NT, that is, $ES_{AV}$, $IS_{AV}$, and $NT_{AV}$ are determined and stored in the output area (step 704).

Then, the average AV (Fingers Average) of measurement points on fingers (e.g., 14 points) for the values ES, IS, and NT, that is, $ES_F$, $IS_F$, and $NT_F$ are determined and stored in the output area (step 705).

Then, the average AV (Toes Average) of measurement points on toes (e.g., 14 points) for each of the values ES, IS, and NT, that is, $ES_T$, $IS_T$, and $NT_T$ are determined and stored in the output area (step 706).

Then, for the value NT, the average AV (Left Average) of measurement points on the left half of the body (e.g., 14 points) $NT_L$ and the average AV (Right Average) of measurement points on the right half of the body (e.g., 14 points) $NT_R$ are determined. Further, the ratio $NT_{L/R}$ between $NT_L$ and $NT_R$ ($NT_L \div NT_R$) is determined. These results are stored in the output area (step 707).

Thus, the diagnostic parameters according to the present invention are obtained.

Embodiment 2

Figure 8:
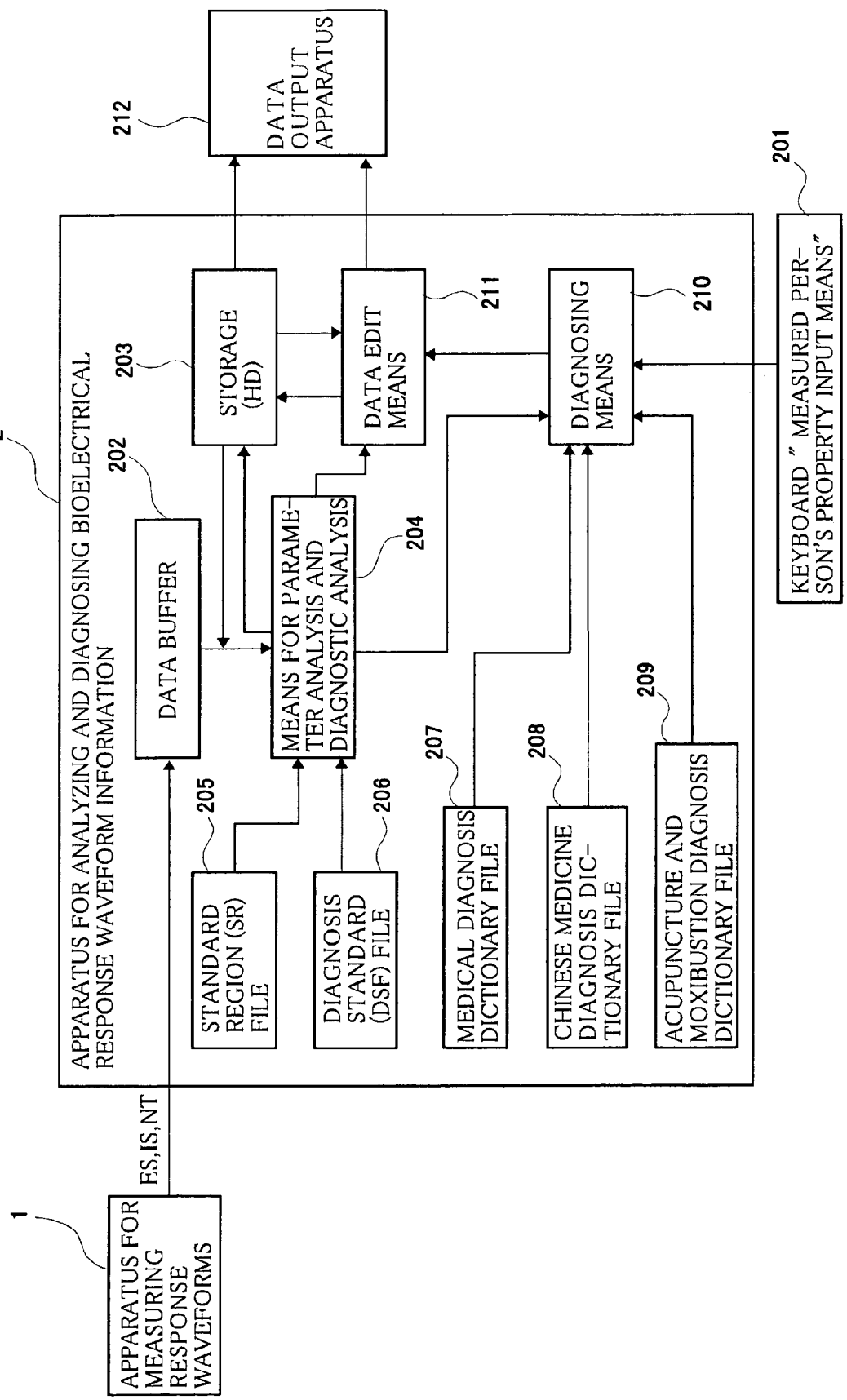
FIG. 8 is a functional block diagram of an apparatus for analyzing and diagnosing bioelectrical response waveform information according to an embodiment (implementation) 2 of the present invention.

FIG. 8 is a functional block diagram of an apparatus for analyzing and diagnosing bioelectrical response waveform information according to an embodiment (implementation) 2 of the present invention.

In FIG. 8, reference numeral 1 denotes an apparatus for measuring response waveforms (apparatus for measuring bioelectrical (skin) impedance), reference numeral 2 denotes the apparatus for analyzing and diagnosing bioelectrical (skin) response waveform information, and reference numeral 212 denotes a data output apparatus.

As shown in FIG. 8, the apparatus for analyzing and diagnosing bioelectrical response waveform information 2 according to the embodiment (implementation) 2 includes: a keyboard 201 for inputting a measured person's properties (a measured person's property input means); a data buffer 202 for storing the three parameter information items of values ES, IS, and NT that are input by the apparatus for measuring response waveforms; storage 203 such as semiconductor memory, an optical disk, or a magnetic disk; means for parameter analysis and diagnostic analysis 204; an SR (Standard Region) file 205; a diagnosis standard file 206, a medical diagnosis dictionary file 207; a Chinese medicine diagnosis dictionary file 208; an acupuncture and moxibustion diagnosis dictionary file 209; diagnosing means 210; and data edit means 211.

Now, a description will be given of diagnosis standards used in the apparatus for analyzing and diagnosing bioelectrical response waveform information according to the embodiment 2, as well as diagnostic operations using the diagnosis standards.

1. Diagnosis Standards

A diagnosis is performed using values obtained from combinations of the three parameters of values ES, IS, and NT. The obtained values may indicate (1) the condition of a whole body, (2) the condition of the respiratory and circulatory system, (3) the condition of each organ system, (4) the conditions of the right side and the left side, and (5) increase or decrease in functionality of each internal organ.

The values ES, IS, and NT of normal people vary due to personal differences. Therefore, for a diagnosis standard, statistical analysis is performed for a population of people considered normal in terms of Western medicine, and the average maximum and minimum values for the most concentrated group region are determined. The range between those values is defined as an SR (Standard Region).

1) Diagnosis on the condition of a whole body indicated by AV (Total Average) of the values ES, IS, NT 1-1-<1>$ES_{AV}$>SR: increase in endocrine and metabolism
1-1-<2>$ES_{AV}$<SR: decrease in endocrine and metabolism
1-1-<3>$IS_{AV}$>SR: increase in immunity, and inflammation
1-1-<4>$IS_{AV}$<SR: decrease in immunity
1-1-<5>$NT_{AV}$>SR: tense sympathetic nerves, pain, and inflammation
1-1-<6>$NT_{AV}$<SR: tense parasympathetic nerves 2) Diagnosis on the condition of the respiratory and circulatory system indicated by AV (Fingers Average) of the values ES, IS, and NT 1-2-<1>$ES_F$>SR: increase in endocrine and metabolism of the respiratory and circulatory system
1-2-<2>$ES_F$<SR: decrease in endocrine and metabolism of the respiratory and circulatory system
1-2-<3>$IS_F$>SR: increase in immunity, and inflammation of the respiratory and circulatory system
1-2-<4>$IS_F$<SR: decrease in immunity of the respiratory and circulatory system 1-2-<5>$NT_F$>SR: tense sympathetic nerves, pain, and inflammation of the respiratory and circulatory system 1-2-<6>$NT_F$<SR: tense parasympathetic nerves of the respiratory and circulatory system 3) Diagnosis on the condition of each organ system indicated by AV (Toes Average) of the values ES, IS, and NT 1-3-<1>$ES_T$>SR: increase in endocrine and metabolism of the organ system 1-3-<2>$ES_T$<SR: decrease in endocrine and metabolism of the organ system 1-3-<3>$IS_T$>SR: increase in immunity, and inflammation of the organ system 1-3-<4>$IS_T$<SR: decrease in immunity of the organ system 1-3-<5>$NT_T$>SR: tense sympathetic nerves, pain, and inflammation of the organ system 1-3-<6>$NT_T$<SR: tense parasympathetic nerves of the organ system 2. Diagnosis based on the ratio between NT of the left half and NT of the right half (left/right) of a body In the description below, the subscript L denotes the average (AV) of the left half of a body with respect to the backbone, and the subscript R denotes that of the right half of the body.

2-1 $NT_L \div NT_R = NT_{L/R} > SR_{L/R}$: abnormal water metabolism 2-1 $NT_L + NT_R = NT_{L/R} < SR_{L/R}$: abnormal blood circulation 3. Diagnosis on each internal organ (from the lung meridian 1 to the bladder meridian 14 at the right and left)

3-1 $ES_{1L \text{ (left 1 to 14)}} + ES_{1R \text{ (right 1 to 14)}} \div 2 = ES_{1A} > SR_{1 \text{ to } 14}$: increase in endocrine and metabolism 3-2 $ES_{1L \text{ (left 1 to 14)}} + ES_{1R \text{ (right 1 to 14)}} \div 2 = ES_{1A} < SR_{1 \text{ to } 14}$: decrease in endocrine and metabolism 3-3 $IS_{1L \text{ (left 1 to 14)}} + IS_{1R \text{ (right 1 to 14)}} \div 2 = IS_{1A} > SR_{1 \text{ to } 14}$: increase in immunity 3-4 $IS_{1L \text{ (left 1 to 14)}} + IS_{1R \text{ (right 1 to 14)}} \div 2 = IS_{1A} < SR_{1 \text{ to } 14}$: decrease in immunity 3-5 $ES_{1L \text{ (left 1 to 14)}} \div ES_{1R \text{ (right 1 to 14)}} = ES_{1L/R} > SR_{L/R1 \text{ to } 14}$: abnormal metabolism 3-6 $ES_{1L \text{ (left 1 to 14)}} \div ES_{1R \text{ (right 1 to 14)}} = ES_{1L/R} < SR_{L/R1 \text{ to } 14}$: abnormal metabolism 3-7 $IS_{1L \text{ (left 1 to 14)}} \div IS_{1R \text{ (right 1 to 14)}} = IS_{1L/R} > SR_{L/R1 \text{ to } 14}$: acute disease 3-8 $IS_{1L \text{ (left 1 to 14)}} \div IS_{1R \text{ (right 1 to 14)}} = IS_{1L/R} < SR_{L/R1 \text{ to } 14}$: chronic disease 3-9 $NT_{1L \text{ (left 1 to 14)}} \div NT_{1R \text{ (right 1 to 14)}} = NT_{1L/R} > SR_{L/R1 \text{ to } 14}$: increase in physiology 3-10 $NT_{1L \text{ (left 1 to 14)}} \div NT_{1R \text{ (right 1 to 14)}} = NT_{1L/R} < SR_{L/R1 \text{ to } 14}$: decrease in physiology.

Figure 9:
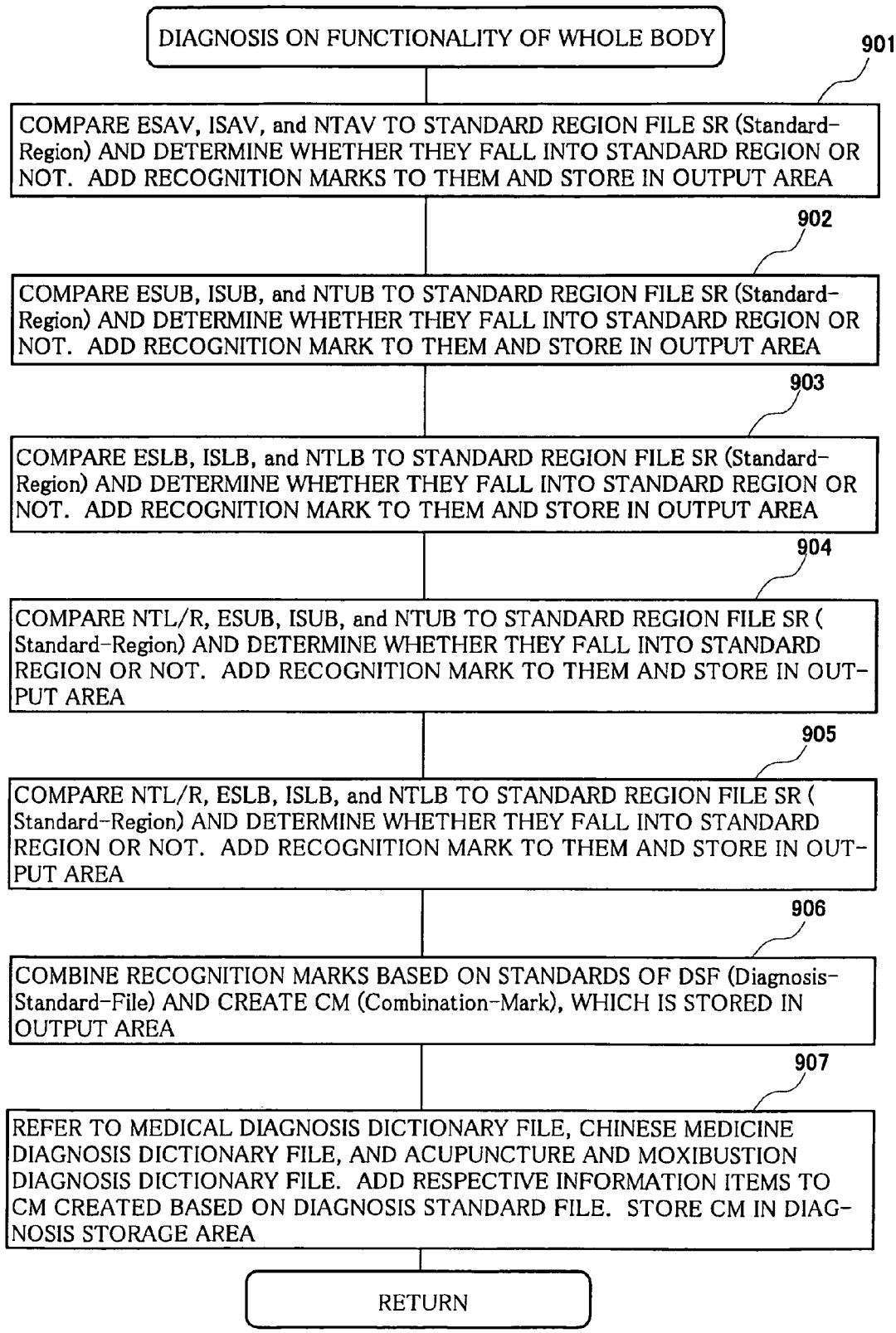
FIG. 9 is a flowchart showing the steps for performing a diagnosis on functionality of a whole body according to the embodiment 2.

Now, the steps for performing a diagnosis on functionality of a whole body will be described with reference to FIG. 9.

First, the values $ES_{AV}$, $IS_{AV}$, and $NT_{AV}$ are compared to the standard region file SR to determine whether they fall into respective standard regions or not. Each of them is given a recognition mark and stored in the output area (step 901).

In the same manner, the values $ES_{UB}$ (UB: Upper Body), $IS_{UB}$, and $NT_{UB}$ for the upper body are compared to the standard region file SR to determine whether they fall into respective standard regions or not. Each of them is given a recognition mark and stored in the output area (step 902).

In the same manner, the values $ES_{LB}$ (LB: Lower Body), $IS_{LB}$, and $NT_{LB}$ for the lower body are compared to the standard region file SR to determine whether they fall into respective standard regions or not. Each of them is given a recognition mark and stored in the output area (step 903).

In the same manner, the value $NT_{L/R}$ and the values $ES_{UB}$, $IS_{UB}$, and $NT_{UB}$ for the upper body are compared to the standard region file SR to determine whether they fall into respective standard regions or not. Each of them is given recognition mark and stored in the output area (step 904).

In the same manner, the value $NT_{L/R}$ and the values $ES_{LB}$, $IS_{LB}$, and $NT_{LB}$ for the lower body are compared to the standard region file SR to determine whether they fall into respective standard regions or not. Each of them is given a recognition mark and stored in the output area (step 905).

Then, based on the standards of the DSF (Diagnosis Standard File), the recognition marks are combined to create a CM (Combination Mark). The CM is stored in the output area (step 906).

Then, reference is made to the diagnosis standard file 206, the medical diagnosis dictionary file 207, the Chinese medicine diagnosis dictionary file 208, and the acupuncture and moxibustion diagnosis dictionary file 209. Respective information items are added to the CM created based on the diagnosis standard file DSF, and the CM is stored in a diagnosis storage area (step 907).

Figure 10:
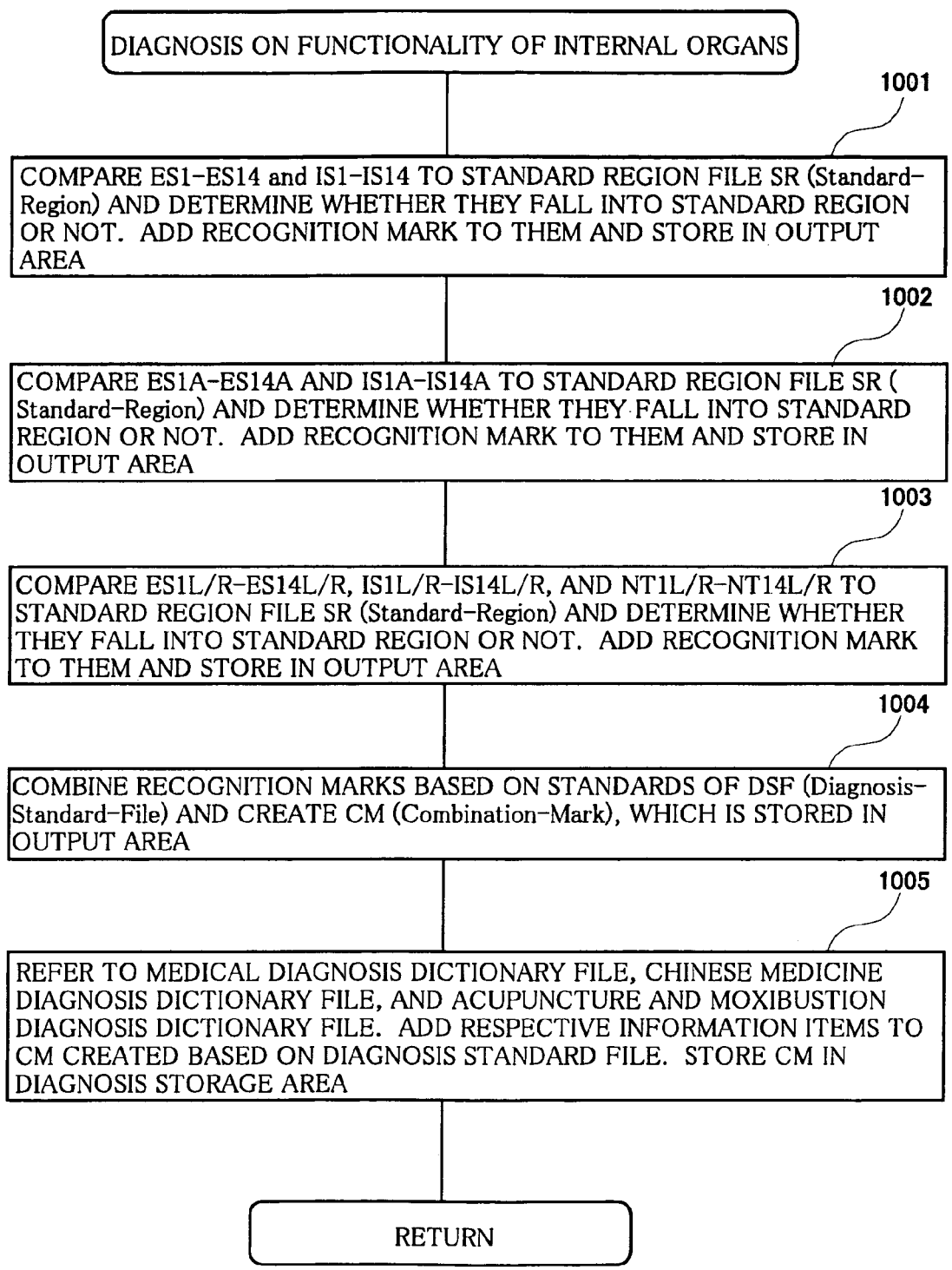
FIG. 10 is a flowchart showing the steps for performing a diagnosis on functionality of internal organs according to the embodiment 2.

Now, the steps for diagnosing functionality of internal organs will be described with reference to FIG. 10.

First, the values $ES_1$ to $ES_{14}$ and $IS_1$ to $IS_{14}$, for example, are compared to the standard region file SR to determine whether they fall into respective standard regions or not. Each of them is given a recognition mark and stored in the output area (step 1001).

In the same manner, the values $ES_{1A}$ to $ES_{14}A$ and $IS_{1A}$ to $IS_{14A}$ are compared to the standard region file SR to determine whether they fall into respective standard regions or not. Each of them is given a recognition mark and stored in the output area (step 1002).

In the same manner, the values $ES_{1L/R}$ to $ES_{14L/R}$, $IS_{1L/R}$ to $IS_{14L/R}$, and $NT_{1L/R}$ to $NT_{14L/R}$ are compared to the standard region file SR to determine whether they fall into respective standard regions or not. Each of them is given a recognition mark and stored in the output area (step 1003).

Then, based on the standards of the DSF (Diagnosis Standard File), the recognition marks are combined to create a CM (Combination Mark). The CM is stored in the output area (step 1004).

Then, reference is made to the diagnosis standard file 206, the medical diagnosis dictionary file 207, the Chinese medicine diagnosis dictionary file 208, and the acupuncture and moxibustion diagnosis dictionary file 209. Respective information items are added to the CM created based on the diagnosis standard file DSF, and the CM is stored in the diagnosis storage area (step 1005).

Figure 11:
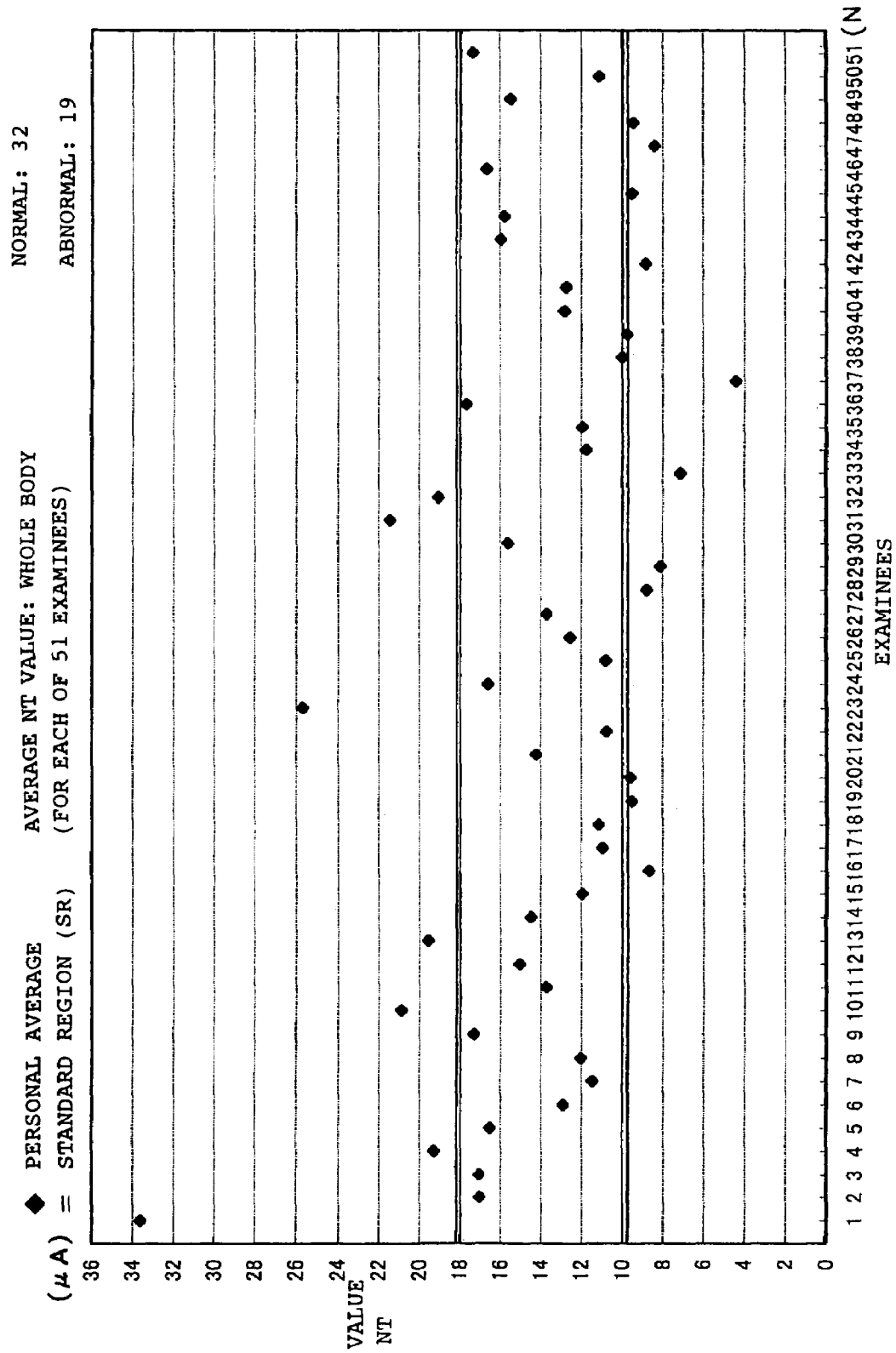
FIG. 11 is a diagram showing average NT values resulted from waveform analysis of a whole body according to the embodiment 2.
Figure 12:
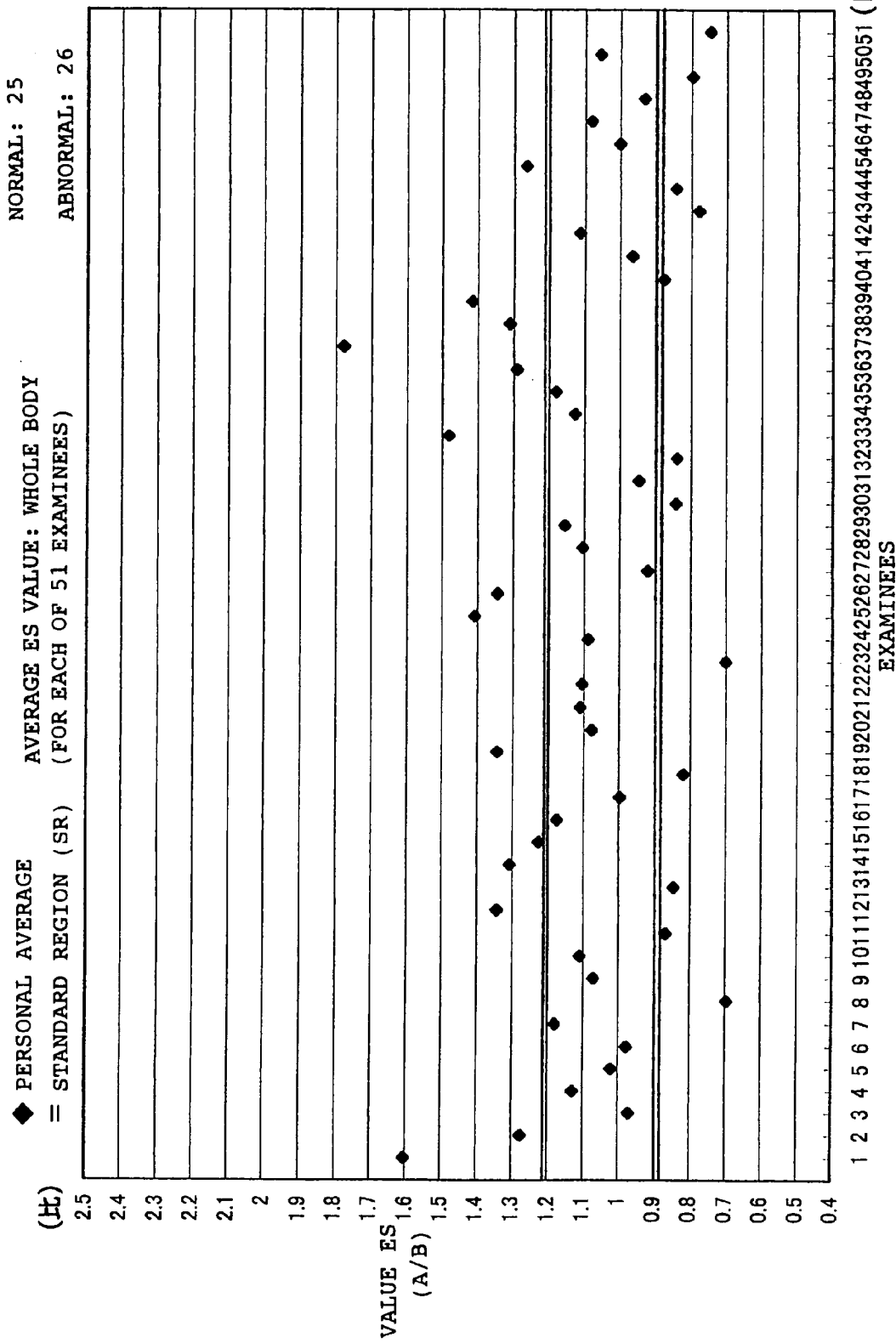
FIG. 12 is a diagram showing average ES values resulted from waveform analysis of a whole body according to the embodiment 2.
Figure 13:
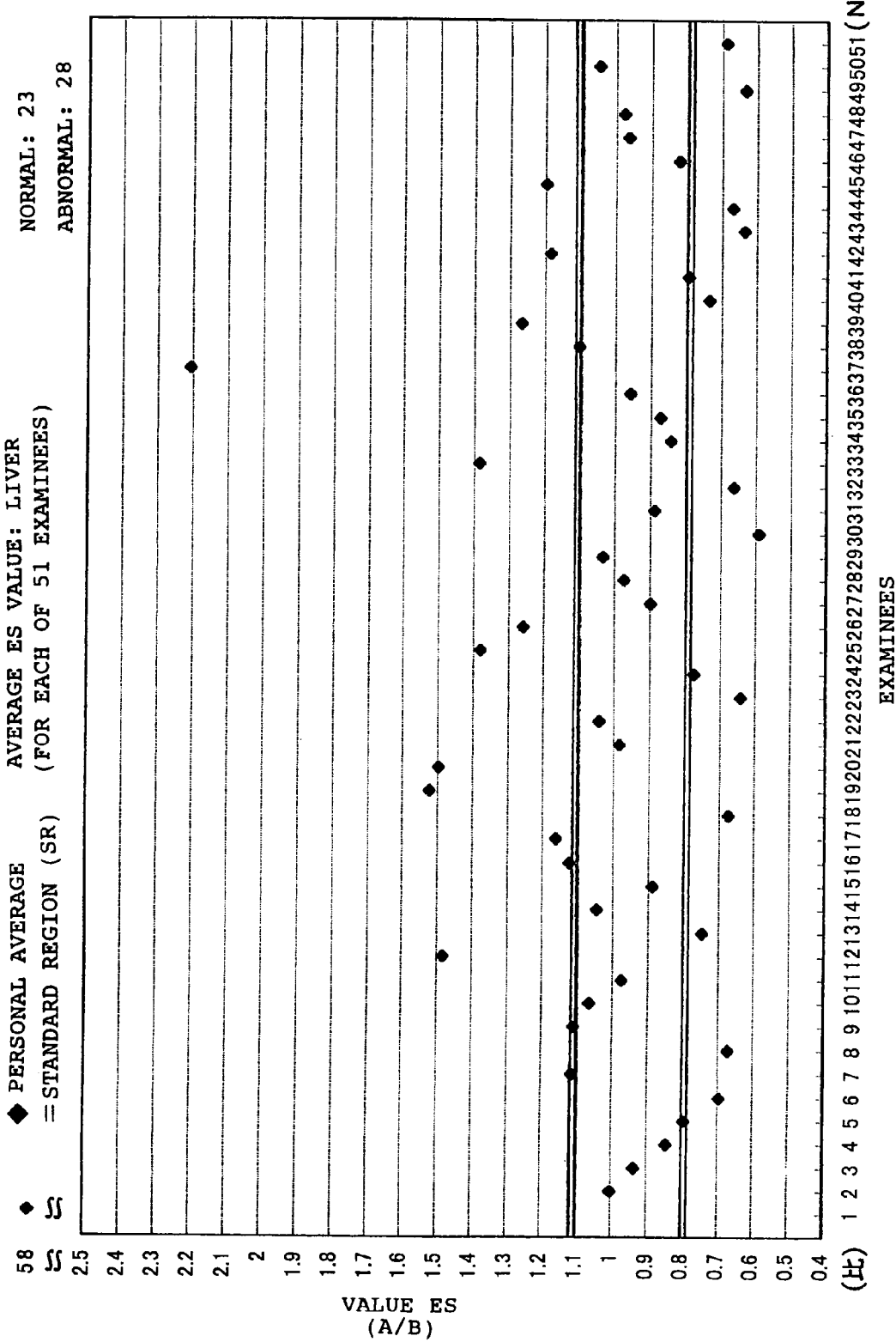
FIG. 13 is a diagram showing average ES values resulted from waveform analysis of the liver meridian according to the embodiment 2.
Figure 14:
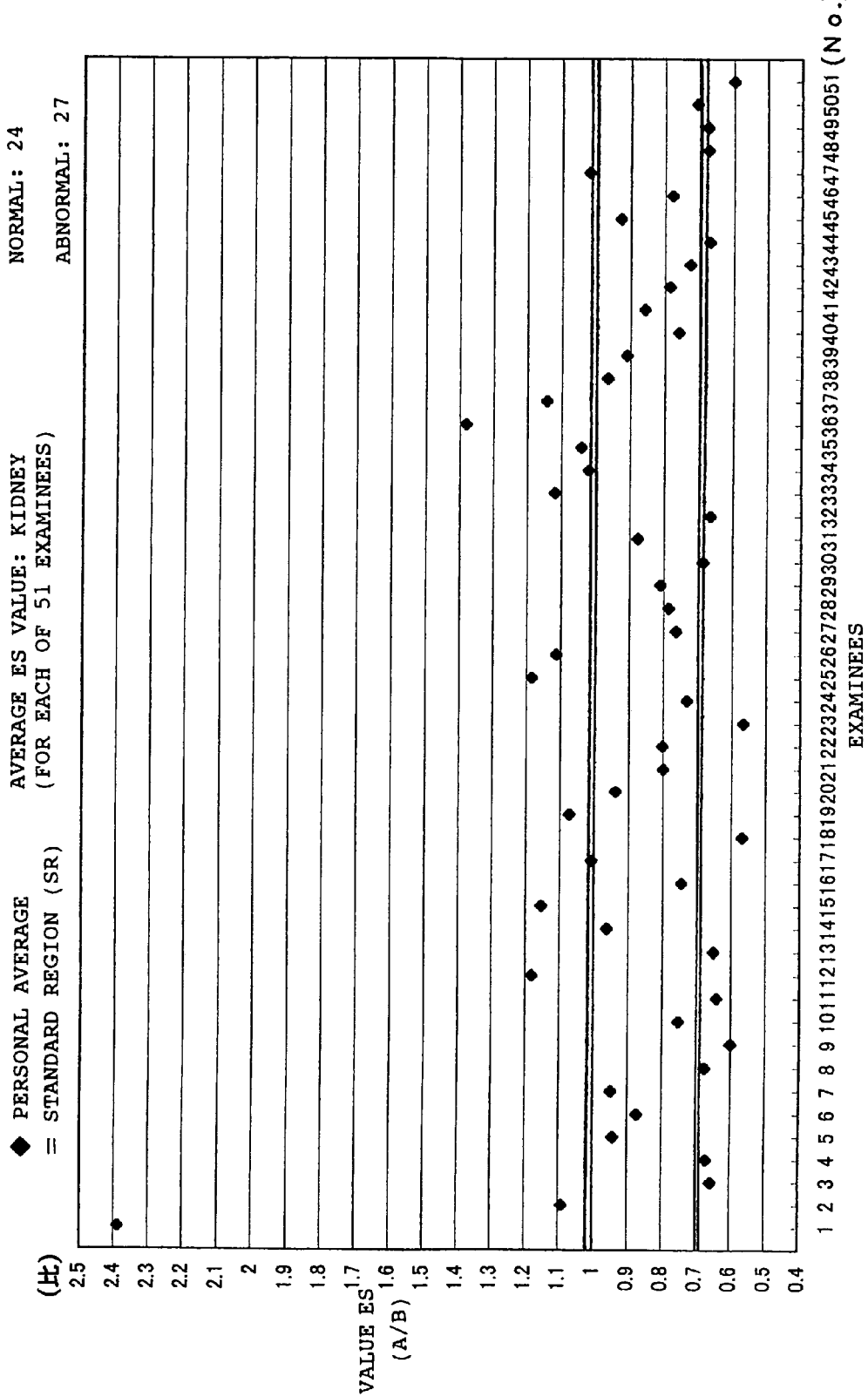
FIG. 14 is a diagram showing average ES values resulted from waveform analysis of the kidney meridian according to the embodiment 2.
Figure 15:
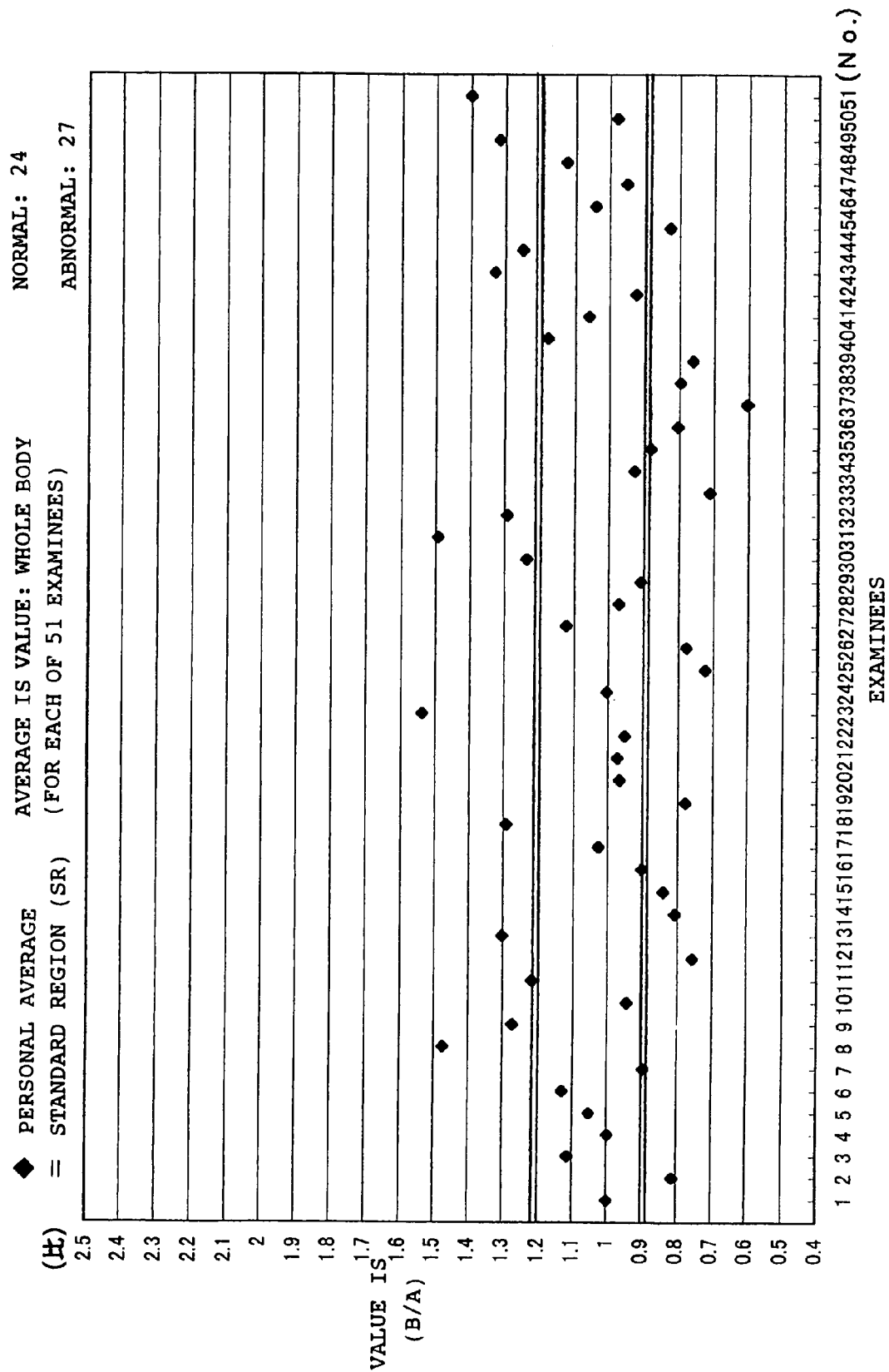
FIG. 15 is a diagram showing average IS values resulted from waveform analysis of a whole body according to the embodiment 2.
Figure 22:
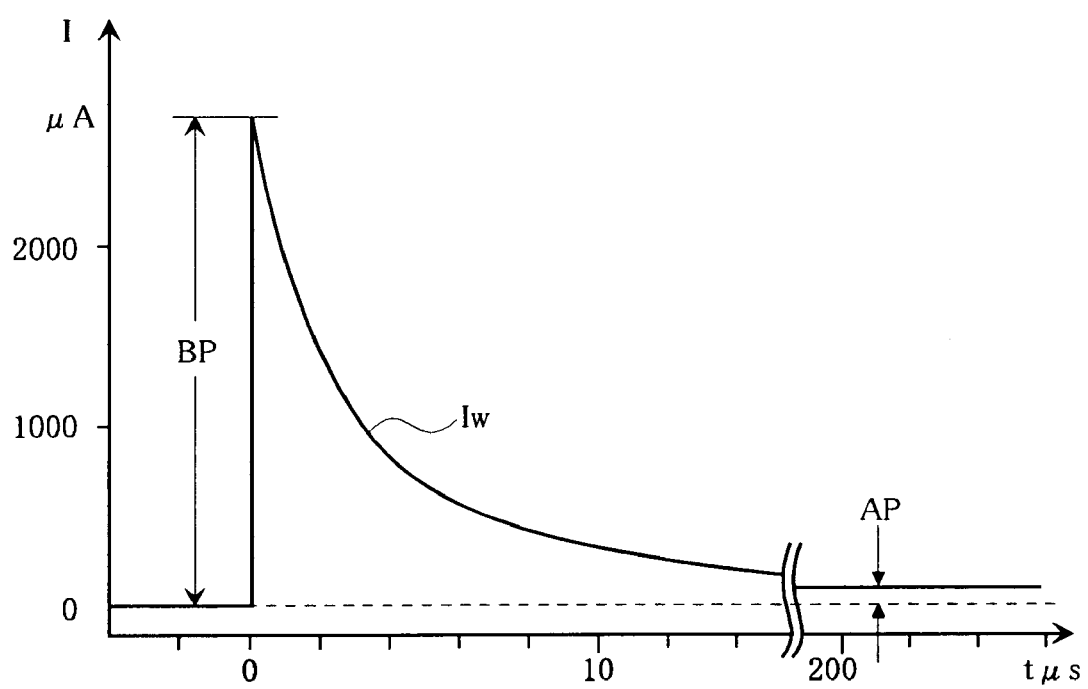
FIG. 22 is a diagram showing a response waveform (current waveform) provided by the conventional apparatus for measuring bioelectrical response waveforms (apparatus for measuring skin impedance).

Analysis for 51 examinees in the embodiment 2 will be shown. FIG. 11 shows average NT values resulted from waveform analysis of a whole body, and FIG. 12 shows average ES values resulted from waveform analysis of a whole body. FIG. 13 shows average ES values resulted from waveform analysis of the liver meridian, and FIG. 14 shows average ES values resulted from waveform analysis of kidney meridian. FIG. 15 shows average IS values resulted from waveform analysis of a whole body, FIG. 16 shows average IS values resulted from waveform analysis of the liver meridian, and FIG. 17 shows average IS values resulted from waveform analysis of the kidney meridian.

As shown in FIGS. 11 to 17, a diagnosis can be performed to determine if an examinee is normal or not with the three parameters of values ES, IS, and NT.

Now, processing for outputting a diagnosis will be described. The diagnosis information on the functionality of a whole body stored in the diagnostic storage area and the diagnosis information on the functionality of internal organs are merged to create personal diagnosis evaluation data. The data may be edited and output as various forms of charts and graphs.

FIG. 18 shows total evaluation for a normal person according to the embodiment 2, as well as the person's clinical examination data in terms of Western medicine.

FIG. 19 shows total evaluation for a diseased person according to the embodiment 2, as well as the person's clinical examination data in terms of Western medicine.

As described, according to the present invention, the three parameters of values ES, IS, and NT are combined to create values that may indicate the condition of the whole body, the condition of the respiratory and circulatory system, the condition of each organ system, the conditions of the right side and the left side, and increase or decrease in functionality of each internal organ. The values can then be used for a diagnosis.

Thus, the present invention has been described with respect to the above embodiments. However, it is to be understood that the invention is not limited to these embodiments but various modification may be made to it without departing from its spirit.

INDUSTRIAL APPLICABILITY

The benefits provided by main aspects of the present invention disclosed herein may be briefly described as follows.

A response waveform provided by an apparatus for measuring bioelectrical response waveforms can be analyzed and computed to produce three parameters of values ES, IS, and NT.

The three parameters of values ES, IS, and NT produced can be combined to perform various diagnoses on patients. The present invention is especially effective when applied to facilitation of an efficient noninvasive primary prophylaxis for keeping health and to a noninvasive medical checkup for diseases.

The invention claimed is:

1. An apparatus for analyzing bioelectrical response waveform information obtained from measurements of skin impedance measured by applying a pulse voltage to a body, the apparatus being characterized by comprising:
   first means for determining a current value P1 at a current peak time when a current is at its peak upon application of the pulse voltage;
   second means for determining a current value P2 after a predetermined amount of time from the current peak time, said predetermined amount of time being an amount of time that elapses before a characteristic point at which a dermis layer and epidermis begin to electrically mix;
   third means for determining a current value NT when the current reaches an equilibrium state with a further elapse of time after the predetermined amount of time;
   fourth means for determining a difference between the current values P1 and P2;
   fifth means for determining a difference between the current values P2 and NT; and
   sixth means for analyzing bioelectrical response waveform information by using three values as parameters, two of the three values, ES and IS, being ratios between the values A and B determined by the fourth and fifth means respectively, where ES=A/B and IS=B/A, and the third value being NT.

2. The apparatus for analyzing bioelectrical response waveform information according to claim 1, characterized in that at least one of the group consisting of: a measurement, an average of measurements, a ratio between measurements of right and left, and a ratio between measurements of hands and feet of bioelectrical response waveform of a body or part of a body; is determined for each of the values ES, IS, and NT.

3. An apparatus for performing a diagnosis on a body wherein the apparatus analyzes bioelectrical response waveform information obtained from measurement of skin impedance measured by applying a pulse voltage to the body and performs a diagnosis based on the analysis of the bioelectrical response waveform information, the apparatus being characterized by comprising:
   first means for determining a current value P1 at a current Peak time when a current is at its peak upon application of the pulse voltage;
   second means for determining a current value P2 after a predetermined amount of time from the current peak time;
   third means for determining a current value NT when the current reaches an equilibrium state with a further elapse of time after the predetermined amount of time from the current peak time;
   fourth means for determining a difference A between the current values P1 and P2;
   fifth means for determining a difference B between the current values P2 and NT;
   sixth means for analyzing bioelectrical response waveform information by using three values as parameters, two of the three values, ES and IS, being ratios between the values A and B determined by the fourth and fifth means respectively, where ES=A/B and IS=B/A, and the third value being NT; and
   seventh means for comparing and associating a result of analysis of the bioelectrical response waveform information outputted from the sixth means with stored clinical examination data.

4. The apparatus for performing a diagnosis on a body based on bioelectrical response waveform information according to claim 3, characterized in that at least one of the group consisting of: a measurement, an average of measurements, a ratio between measurements of right and left, and a ratio between measurements of hands and feet of a bioelectrical response waveform of a body or part of a body; is determined for each of the values ES, IS, and NT.

5. An apparatus for analyzing bioelectrical response waveform information obtained from measurements of skin impedance measured by applying a pulse voltage to a body, the apparatus being characterized by comprising:
   first means for determining a current value P1 at 600 ns, a current Peak time when a current is at its peak upon application of the pulse voltage;
   second means for determining a current value P2 after 4 μs from the current peak time upon application of the pulse voltage, the 4 μs being the time that elapses before a characteristic point at which a dermis layer and epidermis begin to electrically mix;
   third means for determining a current value NT after 256 μs when a current reaches an equilibrium state with a further elapse of time from the current peak time;
   fourth means for determining a difference A between the current values P1 and P2
   fifth means for determining a difference B between the current values P2 and NT; and
   sixth means for analyzing bioelectrical response waveform information by using three values as parameters, two of the three values, ES and IS, being ratios between the values A and B determined by the fourth and fifth means respectively, where ES=A/B and IS=B/A, and the third value being NT.

6. The apparatus for analyzing bioelectrical response waveform information according to claim 5, characterized in that at least one of the group consisting of: a measurement, an average of measurements, a ratio between measurements of right and left, and a ratio between measurements of hands and feet of a bioelectrical response waveform of a body or part of a body; is determined for each of the values ES, IS, and NT.

7. An apparatus for performing a diagnosis on a body wherein the apparatus analyzes bioelectrical response waveform information obtained from measurements of skin impedance measured by applying a pulse voltage to the body and performing a diagnosis on the body based on the analysis of the bioelectrical response waveform information, the apparatus being characterized by comprising:

first means for determining a current value P1 at 600 ns, a current peak time when a current is at its peak upon application of the pulse voltage;

second means for determining a current value P2 after 4 μs from the current peak time, upon application of the pulse the 4 μs being the time that elapses before a characteristic point at which a dermis layer and epidermis begin to electrically mix;

third means for determining a current value NT after 256 μs when the current reaches an equilibrium state with a further elapse of time from the current peak time;

fourth means for determining a difference A between the current values P1 and P2;

fifth means for determining a difference B between the current values P2 and NT;

sixth means for analyzing bioelectrical response waveform information by using three values as parameters, two of the three values, ES and IS, being ratios between the values A and B determined by the fourth and fifth means respectively, where ES=A/B and IS=B/A, and the third value being NT; and seventh means for comparing and associating a result of analysis of the bioelectrical response waveform information outputted from the sixth means with stored clinical examination data.

8. The apparatus for performing a diagnosis on a body based on bioelectrical response waveform information according to claim 7, characterized in that at least one of the group consisting of: a measurement, an average of measurements, a ratio between measurements of right and left, and a ratio between measurements of hands and feet of a bioelectrical response waveform of a body or part of a body; is determined for each of the values ES, IS, and NT.

* * * * *